(12) United States Patent
Zamoyski

(10) Patent No.: US 7,507,704 B1
(45) Date of Patent: Mar. 24, 2009

(54) RECEPTOR MODULATED CANCER PROTOCOLS

(76) Inventor: Mark Zamoyski, 988 Foothill Dr., San Jose, CA (US) 95123-5301

( * ) Notice: Subject to any disclaimer, the term of this patent is extended or adjusted under 35 U.S.C. 154(b) by 68 days.

(21) Appl. No.: 11/809,264

(22) Filed: May 30, 2007

Related U.S. Application Data

(63) Continuation-in-part of application No. 10/295,600, filed on Nov. 15, 2002, now Pat. No. 7,309,486.

(51) Int. Cl.
*A01N 61/00* (2006.01)
*A61K 39/00* (2006.01)

(52) U.S. Cl. .......................... 514/1; 424/198.1
(58) Field of Classification Search .............. 514/1
See application file for complete search history.

(56) References Cited

U.S. PATENT DOCUMENTS 6,486,146 B1    11/2002    Zamoyski

OTHER PUBLICATIONS

Tarceva®erlotinib tablets, full prescribing information, Genetech Inc. and OSI Pharmaceuticals, Rev. Nov. 2, 2005.
Erbitux® (Cetuximab), full prescribing information, ImClone Systems Inc. and Bristol-Myers Squibb, Mar. 2006.
Iressa® gefitinib tablets, full prescribing information, AstraZeneca Pharmaceuticals Inc., Rev. Jun. 2005.
Vectibix™ (panitumumab), full prescribing information, Amgen Inc.
Herceptin®trastuzumab, full prescribing information, Genentech Inc., Rev. Nov. 2006.
Avastin® (bevacizumab), full prescribing information, Genetech Inc., Rev. Oct. 2006.
Harrison's Principles of Internal Medicine, 15th Edition, McGraw-Hill Medical Publishing Division, pp. 538-541.
Lisa M. Misell,et. al. "Development of a novel method for measuring in vivo breast epithelial proliferation in humans", Breast Cancer Research and Treatment (2005) 89:257-264.
Lippman et.al., J Clin Onc., vol. 2, No. 1 Jan. 1984 A Randomized Attempt to Increase Efficacy of Cytotoxic Chemotherapy in Metastatic Breast Cancer by Hormonal Synchronizati.
Shapiro et. al. J Clin Oncol., Jul. 15, 2001;19(14): 3306-11 Ovarian Failure after adjuvant chemotherapy is associated with rapid bone loss in woman with early-stage breast can.
Aromasin® exemestane tablets, full prescribing information, Pfizer and Pharmacia & Upjohn Company, Feb. 2007 revision.
Zoladex® Goserelin Acetate Implant, full prescribing information, AstraZeneca, rev. Oct. 2005.
Vibeke Bech Thogersen et. al., Cancer Research 61,6227-6233, Aug. 15, 2001, ". . . HER1 Ligands . . . .".

*Primary Examiner*—Sean E Aeder

(57) ABSTRACT

The present invention discloses that prior art protocols that administer HER receptor blockers concurrently with phase specific cytotoxic chemotherapeutics result in antagonistic function that prevents subsequent administrations of phase specific cytotoxic from functioning. The present invention provides protocols that allow the two classes of drugs to function synergistically. Moreover, the present invention also identifies that gompertzian tumor growth results in heterogeneity of cell cycle times in a tumor and that chemotherapeutic depopulation of the tumor results in accelerating cell cycle times, both of which preclude synchronicity of successive administrations of S-Phase cytotoxics relative to the progression of the S-Phase in the cancer cell population under prior art protocols. Present invention provides novel "synchronous" protocols for S-Phase cytotoxics, using HER blockers, to overcome this problem. Present invention also discloses how to integrate protocols of U.S. Pat. No. 6,486,146 for HER+ cancers that are also endocrine dependent.

7 Claims, 20 Drawing Sheets

Restricted Blood Flow Stasis Region

Density Dependent Inhibition Pathways Stasis Region

Growth Factor Deficit Stasis Region

Endocrine Hormone Deficit Stasis Region

Endocrine Hormone Deficit Aggregation Region

One Day of Non Tumor Specific S-Phase Aggregation
(for a 20 day PDT tumor)

Pre-Treatment

Administration of Endocrine(s)

Administration of S-Phase Cytotoxic

Aggregation Period

Administration of Endocrine(s)

Administration of S-Phase Cytotoxic

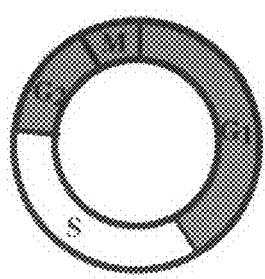
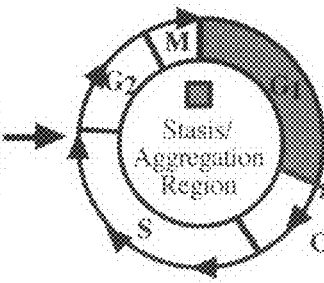
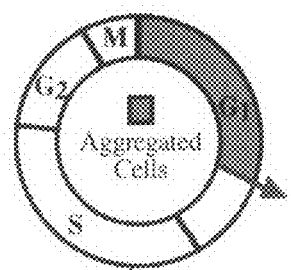

1) First Administration of S-Phase Cytotoxic Kills S-Phase Cells

2) Receptor Inhibitor Aggregates Remaining Cells in the G1-Phase

3) Subsequent S-Phase Cytotoxic Administrations do not work because of S-Phase depletion FIG. 19a       FIG. 19b       FIG. 19c

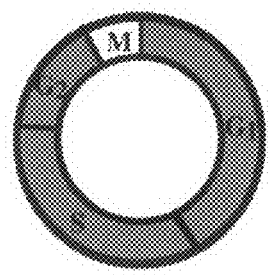
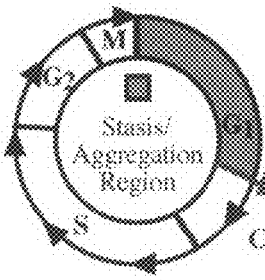
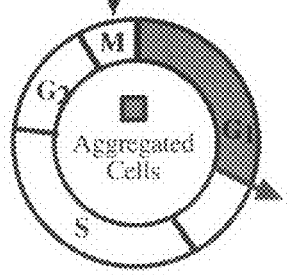

1) First Administration of M-Phase Cytotoxic Kills M-Phase Cells

2) Receptor Inhibitor Aggregates Remaining Cells in the G1-Phase

3) Subsequent M-Phase Cytotoxic Administrations do not work because of M-Phase depletion FIG. 19d       FIG. 19e       FIG. 19f

RECEPTOR MODULATED CANCER PROTOCOLS

CROSS REFERENCE TO RELATED APPLICATIONS

This application is a CIP of application Ser. No. 10/295,600 now U.S. Pat. No. 7,309,486 filed Nov. 15, 2002 for chemotherapy protocols employing combinations of HER2 receptor blockers and phase specific, cell cycle active cytotoxic chemotherapy. The parent application disclosed that prior art protocols that concurrently administered receptor blockers and phase specific cytotoxics were antagonistic and novel protocols were provided for synergistic receptor blocker/S-Phase cytotoxic combinations. Trastuzumab (a HER2 receptor blocker) was used as a representative growth factor receptor inhibitor in the examples of the parent application and the scope of the application was intended to encompass the use of any growth factor receptor inhibitor and any S-Phase cytotoxic under the novel protocols disclosed. However, the USPTO held that the claims needed to be limited only to HER2 receptors used in the representative examples. Accordingly, this CIP application provides additional examples, using HER1 growth factor receptor blockers, to expand the scope of the claims to those originally intended under the parent application.

STATEMENT REGARDING FEDERALLY SPONSORED RESEARCH

Not Applicable.

INCORPORATION-BY-REFERENCE OF MATERIAL SUBMITTED ON A CD

Not Applicable

BACKGROUND OF THE INVENTION

1. Field of the Invention

The invention relates to composition and methods for the treatment of cancer, and in particular for protocols for combination chemotherapy. More specifically, the patent application deals with protocols that combine growth factor receptor inhibitors (also referred to as receptor blockers or growth factor blockers) with phase specific cell cycle active cytotoxic chemotherapeutics.

A big part of the problem with prior art protocols that use growth factor receptor inhibitors in combination with phase specific cell cycle active cytotoxic chemotherapeutics is that prior art practitioners do not even realize there is a problem. Receptor inhibitors are used concurrently with phase specific cytotoxics, as stipulated in their full prescribing information, and these protocols are summarized in the specification section of this application. Applicant will show why this is a problem. In summary, the prior art protocols result in antagonistic function, wherein only the first administration of phase specific cytotoxic chemotherapy works, and all subsequent administrations result only in systemic toxicity with no therapeutic benefit. Doing harm (systemic toxicity), without therapeutic benefit, is a violation of medical ethics. Accordingly, a compelling case can be made that the major receptor inhibitor manufacturers (e.g. Genentech, ImClone/Bristol Myers, AstraZeneca, etc. . . . ) are not aware of the problem.

Applicant will outline the mechanisms of action related to why prior art protocols have a problem. Applicant will also provide clinical corroboration of the problem, including using Genentech's own Phase III human data. Applicant will then propose novel protocols that result in synergistic function, whereby a much better treatment method will by provided.

2. Description of Related Art

The curative value of chemotherapy as used under prior art is minimal at best. Advanced stage cancers, which rely primarily on chemotherapy for a cure, indicate just how modest chemotherapy's contribution is under prior art: the 5 year survival rate for Stage 1V metastatic lung cancer is 1%, Stage 1V metastatic colon cancer is 5%, pancreatic cancer is 2%, and Stage 1V metastatic breast cancer is 14% (Harrison's 15th ed. pgs. 565, 584, 591, 575 respectively). Prior art chemotherapy only extends median survival by a few months of misery.

There are around 50 chemotherapeutic agents available for use today. Most of them are cell cycle active cytotoxic, meaning they kill actively proliferating cells. Most of these chemotherapeutics are cytotoxic during a given phase of the cell cycle (i.e. phase specific). Of the chemotherapeutics listed in Harrison's Principles of Internal Medicine, 15th. edition, pgs. 538-541, roughly 60% are S-Phase specific and 14% are M-Phase specific.

A brief review of currently used chemotherapeutics is presented for reference.

Topoisomerase inhibitors induce cytotoxicity by interfering with the enzymes topoisomerase 1 and topoisomerase 2. DNA replication results in torsional strain that, if not relieved by topoisomerase, results in DNA strand breakage. Topoisomerase 1 inhibitors include irinotecan, topotecan, and camptothecin. Topoisomerase 2 inhibitors include epipodophyllotoxins such as etoposide and teniposide and anthracyclines such as daunorubicin, doxorubicin, and idarubicin. Topoisomerase inhibitors are S-Phase specific.

Antimetabolites induce cytotoxicity by serving as false substrates in biochemical pathways. Pyrimidine analogs include cytarabine, fluorouracil (5 FU), and gemcitabine. Purine analogs include cladribine, fludarabine, and pentostatin. Other antimetabolites include hydroxyurea and methotrexate. They are S-Phase specific.

Alkylating agents are efficient at cross-linking DNA, leading to strand breakage. Alkylating agents include cyclophosphamide, ifosfamide, melphalan, busulfan, mechlorethamine (nitrogen mustard), chlorambucil, thiotepa, carmustine, lomustine as well as platinum compounds such as cisplatin and carboplatin, which are not true alkylating agents also lead to covalent cross linking of DNA. These agents are classified as non-phase specific.

Plant Alkaloids include vincristine, vinblastine, and vinorelbine which inhibit microtubule assembly by binding to tubulin and docetaxel and paclitaxel which function by stabilizing microtubules and preventing their disassembly. They are cell cycle active and cytotoxic predominately during the M phase of the cell cycle.

Bleomycin induces DNA strand breakage through free radical generation and is cytotoxic mainly during the G2 and M phase. Mitomycin C cross links DNA.

Other Agents include dacarbazine and procarbazine which act as alkylating agents to damage DNA and L-Asparaginase, the only enzyme used as a anti tumor agent, which acts by depletion of extracellular pools of asparagine.

Imatinib (Gleevec from Novartis) functions as an inhibitor of a number of tyrosine kinase enzymes by binding to the kinase domain.

Growth Factor Receptor Inhibitors (receptor blockers) target specific growth factor receptors and prevent their activation. Commercially available receptor blockers include receptor monoclonal antibodies (MAbs) and small molecule receptor inhibitors. MAb receptor inhibitors commercially available are Trastuzumab (Genentech's Herceptin) which is a HER2 antibody and cetuximab (ImClone's Erbitux) and panitumumab (Amgen's Vectibix) which are a HER1 (EGFR) antibodies. Small molecule receptor inhibitors commercially available include gefitinib (AstraZeneca's Iressa) and erlotinib (Genentech's tarceva), both of which are HER1 blockers.

Angiogenesis Inhibitors do not directly target the cancer cells but function indirectly by inhibiting blood vessel (endothelial cell) growth in tumors and include drugs such as Bevacizumab (Genentech's Avastin®) which is a antibody that binds to VEGF and numerous other angiogenesis inhibitors are currently in clinical trials.

Protocols for administering cell cycle active chemotherapy were developed, in many cases, decades ago under concepts of "maximum tolerated doses" which were primarily designed to allow for recovery from systemic toxicity. Traditional "legacy protocols" administer a dose of chemotherapy every 7 or 21 days for several cycles. Higher frequency protocols administer chemotherapy at lower doses every day for 3-5 days for several cycles or at ultra low doses every day for up to 21 days (Harrison's Principles of Internal Medicine, 15th. edition, pgs. 538-541).

Angiogenesis inhibitors are administered continually over the course of a chemotherapeutic regimen and they have been able to further extend median survival by 2 to 5 months, depending on cancer type (per Genentech's Avastin full prescribing information).

Growth factor receptor blockers have come on the scene over the last several years. They are administered either as a single agent treatment option or are administered concurrently with conventional chemotherapeutic regimens. The combination receptor blocker/conventional chemotherapy protocols are the topic of present invention.

BRIEF SUMMARY OF THE INVENTION

The present application discloses that prior art combination receptor blocker/Phase specific cytotoxic protocols are antagonistic and novel protocols are provided for synergistic receptor blocker/S-Phase cytotoxic combinations. Simplistically, prior art's continues administration of receptor blocker over the regimen results in S-Phase and M-Phase depletion, which prevents function of all but the first administration of S-Phase and M-Phase cytotoxics. Novel protocols are proposed that use interlaced administrations of receptor blocker to provide synergistic function. Furthermore, novel protocols are presented that progressively eliminate density related stasis points and prevent their reestablishment so that a homogeneously cycling tumor may be created. A homogeneously cycling tumor is easy to eradicate using S-Phase cytotoxics.

BRIEF DESCRIPTION OF THE DRAWINGS

FIGS. 19a through 19f show the phase distribution of tumor cells during a prior art antagonistic regimen using a receptor blocker concurrent with an S-Phase cytotoxic and 19d through 19e show the phase distribution when using the same with an M-Phase cytotoxic.

DETAILED DESCRIPTION OF THE INVENTION

Figure 1:
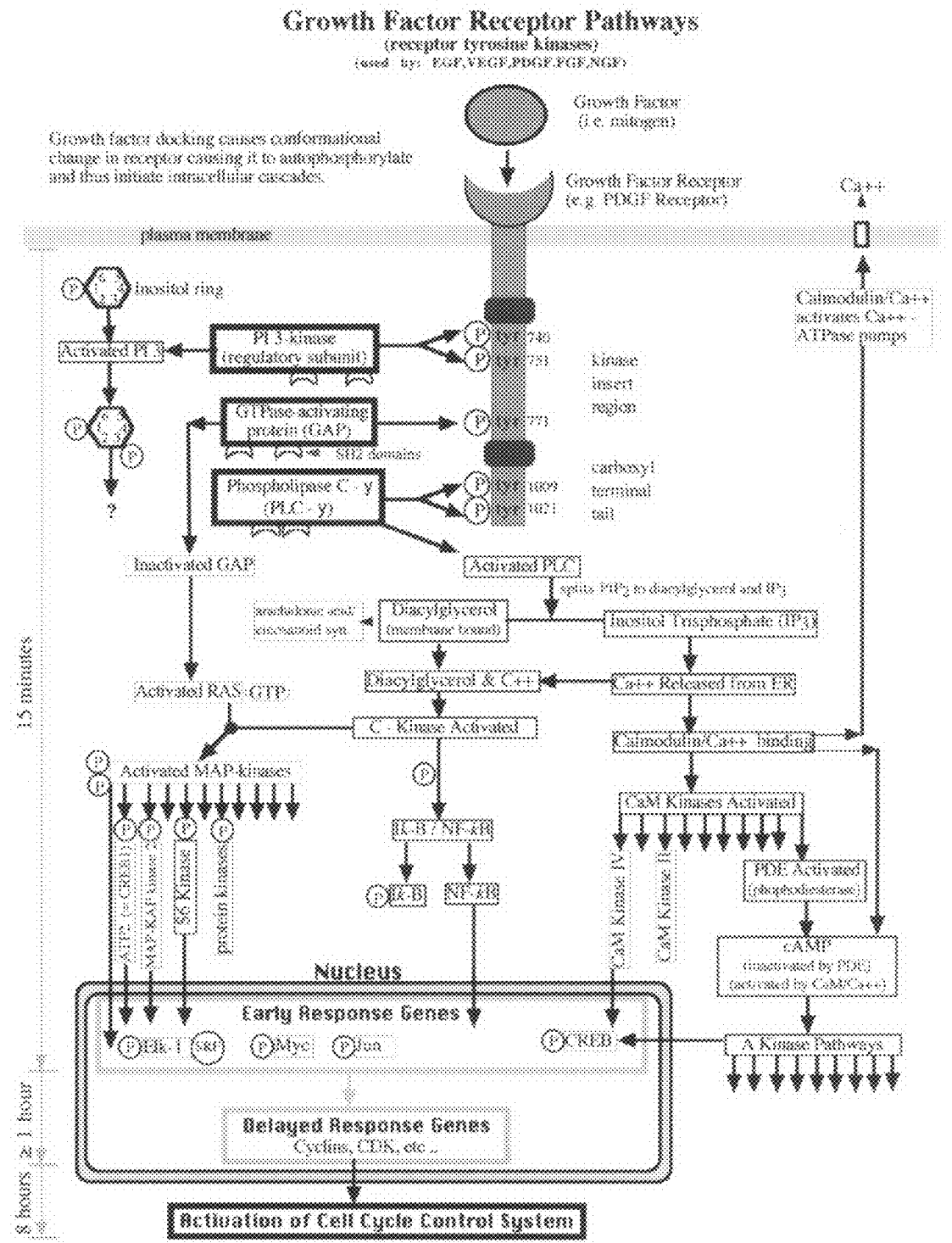
FIG. 1 shows growth factor receptor pathways leading to activation of the cell cycle control system.

Overview:

To understand the invention, it is first necessary to understand why prior art's "legacy protocols" don't cure cancer but only yield a modest increase in median survival.

Second, it is necessary to understand why prior art attempts at phase enrichment and phase synchronization failed and what is required to achieve usable phase synchronous regimens that are Skipper compliant.

Third, it is necessary to understand why receptor blockers are antagonistic to S-Phase or M-Phase cytotoxics when used continuously with legacy protocols, as is done under prior art.

After covering the 3 above points, the invention then discloses novel protocols that use receptor inhibitors synergistically, and provide a novel approach to treatment of cancer with chemotherapy.

1) Why Prior Art Legacy Protocols Fail to Cure Cancer

In summary, prior art cell cycle active, phase specific chemotherapeutic administrations fail to remain synchronous to the progression of the susceptible phase (i.e. the phase in which they exert cytotoxicity) in the cancer cells because of 1) heterogeneity of cell cycle times in a tumor and because of 2) chemotherapeutic induced Gompertzian acceleration in cell cycle times (i.e. de-populating a tumor removes density dependent stasis points). Without synchronicity, curative outcome cannot be expected. A brief description of the underlying Mechanisms of Action (MOA) and Clinical Corroboration from Phase III clinical trials is presented below (originally disclosed in part by applicant in U.S. Pat. No. 6,486,146, incorporated herein by reference in its entirety).

To understand why prior art regimens fail to cure cancer, it is necessary to bring together several areas of science. These include:

A) the molecular biology of growth control pathways and mutations in growth control pathways that result in cancer, B) principles of chemotherapy including the Skipper Log Cell Kill Model, C) kinetics of Gompertzian tumor growth and underlying mechanisms of stasis, and D) why chemotherapy fails to cure cancer in light of Gompertzian kinetics and the Skipper log cell kill model.

A) Molecular Biology of Cancer—Growth Control Pathways:

Cancer starts with the accumulation of several independent genetic accidents (mutations) in growth control pathways, in a single aberrant cell. That aberrant cell, and all of its progeny, are "hard wired" to relentlessly grow and divide (cycle). Growth control pathways are used for population density management. There are around 210 different cell types in the body and cells produce and release protein growth factors (mitogens). Around 50 growth factors are known. Cells also possess combinations of transmembrane growth factor receptors. One end of the receptor is exposed on the cell surface (extracellular domain) and the other side is inside the cell (intracellular domain) When growth factors dock with the extracellular domain of the growth factor receptors, the receptor is activated. This results in activation of intracellular transduction molecules and intracellular cascades that result in activation of transcription factors that in turn result in DNA expression for production of proteins that drive the cell to grow and divide (cycle).

Cells also produce proteins that inhibit growth. Population density is a balance between stimulators (growth factors) and inhibitors of growth.

In cancer, mutations tip the balance in favor of growth.

Known causes of mutations include DNA replication errors during cell division (~3 per division), chemical carcinogens that result in DNA damage, electromagnetic radiation that results in covalent bond breakage, and roughly 15% of cancer mutations trace back to viral origins.

Since mutations in growth control pathways are the underlying cause of cancer, it is important to understand the molecular biology of growth control pathways.

Figure 2:
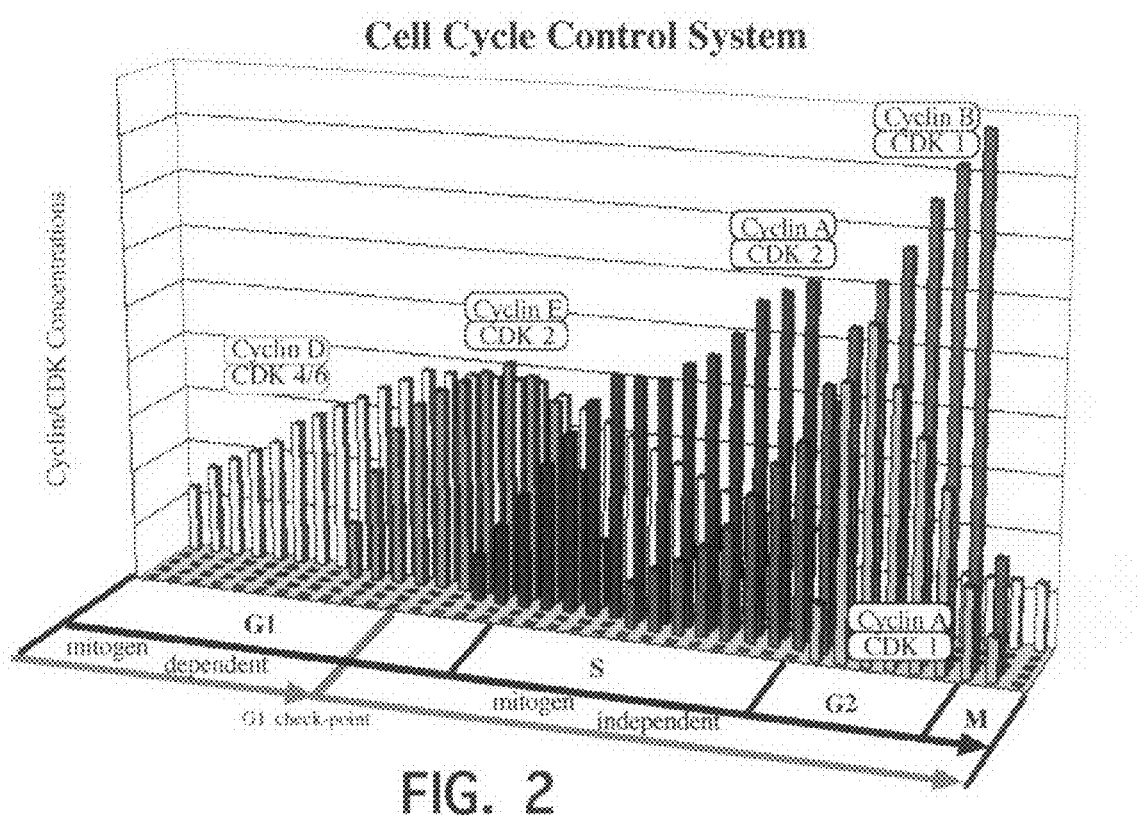
FIG. 2 shows the levels of cyclin/cdk proteins in an activated cell cycle control system.

Growth factor docking with transmembrane growth factor receptors triggers intracellular cascades that result in activation of the "Cell Cycle Control System". A schematized representation of a common growth factor receptor family (receptor tyrosine kinase family) is shown in FIG. 1. Growth factors such as EGF, VEGF, PDGF, FGF, and NGF dock with this receptor type. Growth factor docking with the receptor results in a conformational change in the receptor, causing it to autophosphorylate and initiate intracellular cascades. One of the intracellular cascades results in production of proteins such as Cyclin and CDK that are used to drive the Cell Cycle Control System as shown in FIG. 2. The Cell Cycle Control System guides cell growth and division through the 4 phases of the cell cycle. Cyclin D is environment sensitive, having a half life of only 15 minutes. If mitogen (growth factor) levels drop, Cyclin D levels also drop quickly, preventing the cell from progressing further through the cell cycle. If the cell has already passed the G1 checkpoint, it will continue through the cell cycle despite a drop in mitogen levels.

Figure 3:
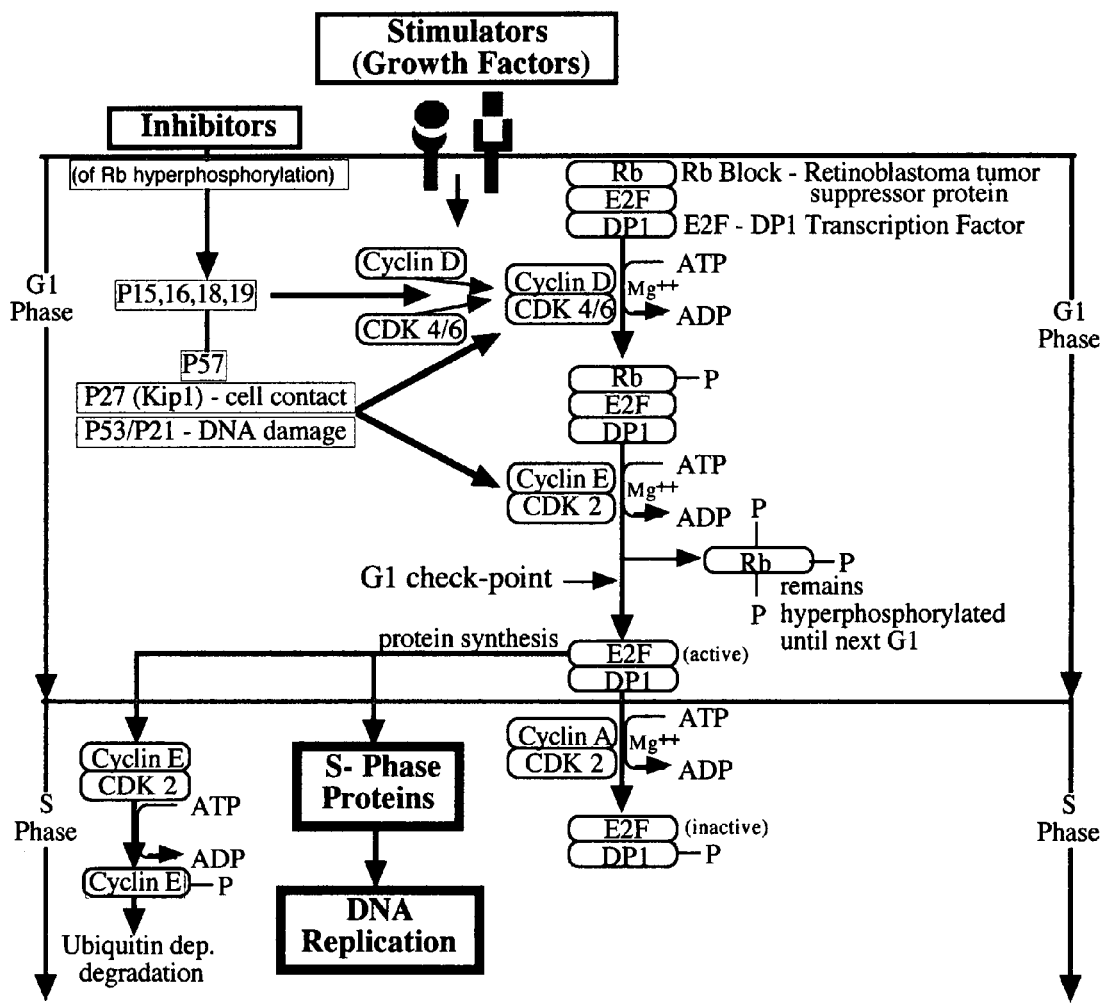
FIG. 3 shows the stimulatory and inhibitory pathways related to the cell cycle control system through the G1 phase.

The early stage Cyclin/CDK complexes (Cyclin D/ CDK 4/6 and Cyclin E/ CDK2) function to activate transcription factors by removing the Rb block. Cells also produce various proteins to inhibit formation or function of the Cyclin/CDK complexes. The balance between stimulators and inhibitors of growth determines whether or not the cell will grow and divide as shown in FIG. 3. If the mitogen stimulation persists long enough and is strong enough to overcome the inhibitors of growth, a cell will grow and divide. Once the G1 checkpoint is reached (i.e. sufficient Rb hyperphosphorylation) the cell is terminally committed to complete the cell cycle.

Figure 4:
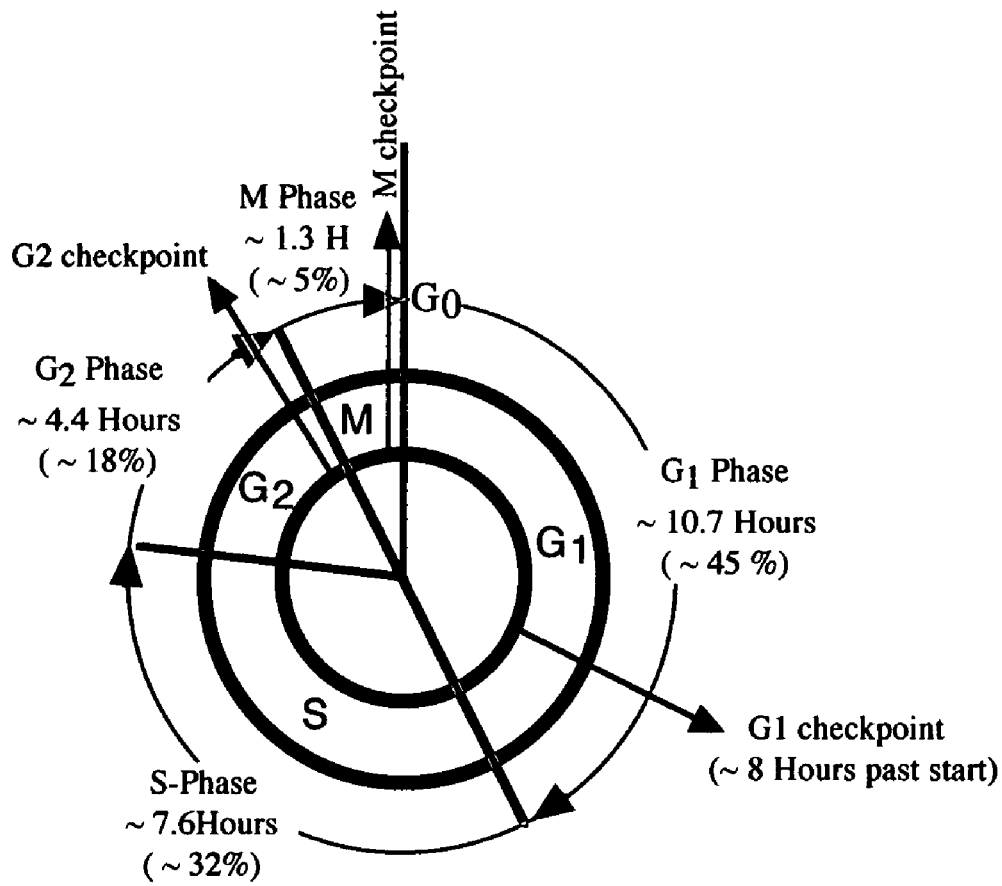
FIG. 4 shows the phase distribution, with checkpoints, for a typical cycling human cell.

The cell cycle has 4 distinct phases termed G1-Phase for "growth 1", S-Phase termed so for "Synthesis of DNA", G2-Phase for "growth 2", and M-Phase for "Mitosis" where the cell divides into two separate cells. The amount of time spent by phase, for a typical 24 hour cell cycle time cell such as bone marrow, is shown in FIG. 4. In a randomly cycling cell population, the amount of time required to progress through the cell cycle is directly proportional to the number of cells that will be in that phase of the cell cycle at any given point in time. As an example, if it takes 32% of the time to progress through the S-Phase of the cell cycle, at any given point in time, roughly 32% of the cells will be in the S-Phase in a randomly cycling population. Likewise, since the M-Phase takes up only 5% of the cell cycle time, only 5% of the cells will be in the M-Phase.

Figure 5:
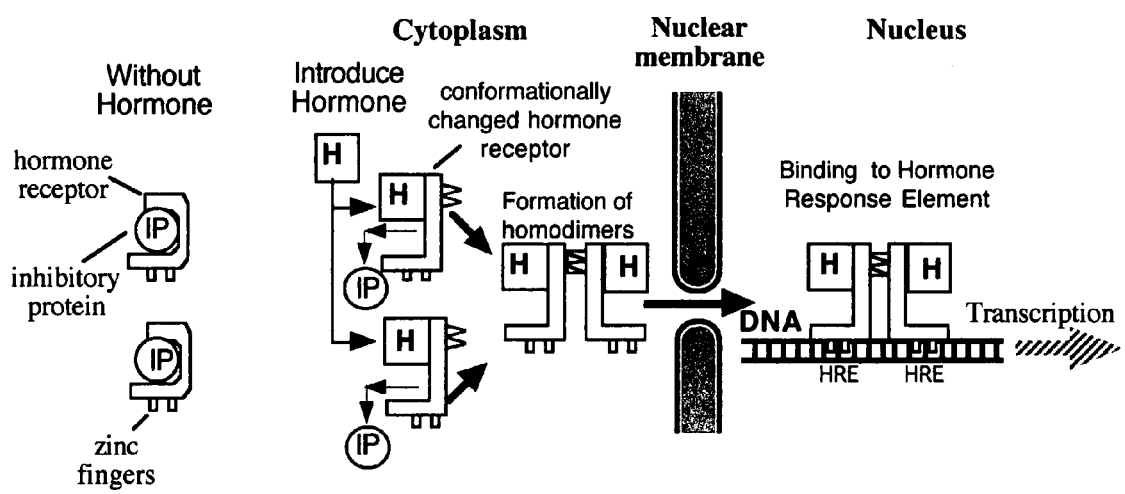
FIG. 5 shows endocrine hormone receptor pathways.

Certain cells in the body have a second set of controls on the cell cycle. In these cells, the progression of the cell into and through the S-Phase of the cell cycle requires the presence of endocrine hormones. Breast cells are often estrogen or progesterone dependent. Prostate cells are testosterone dependent. Endocrines steroid hormones dock with intracellular receptors (in contrast to growth factors that dock with the extracellular domain of transmembrane receptors). A schematized model of an intracellular steroid hormone receptor system is shown in FIG. 5. Endocrine dependence is a trait inherent in the cell type and is often retained by malignant cells. Endocrines such as estrogen and progesterone are produced primarily in the ovaries in pre menopausal women (circulating estrogen in post menopausal women is from conversion of adrenal and ovarian androgens by aromatase). Testosterone is produced primarily in the testes.

Figure 6A:
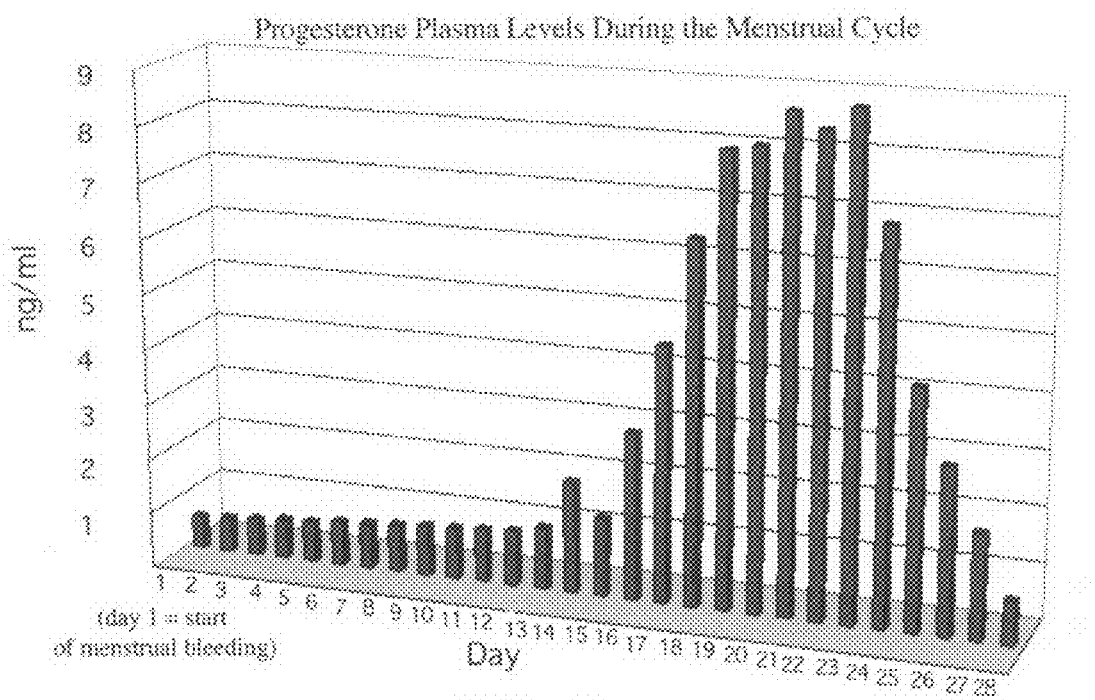
FIGS. 6a and 6b show the fluctuations in progesterone and estrogen levels during the ovulation cycle.
Figure 6B:
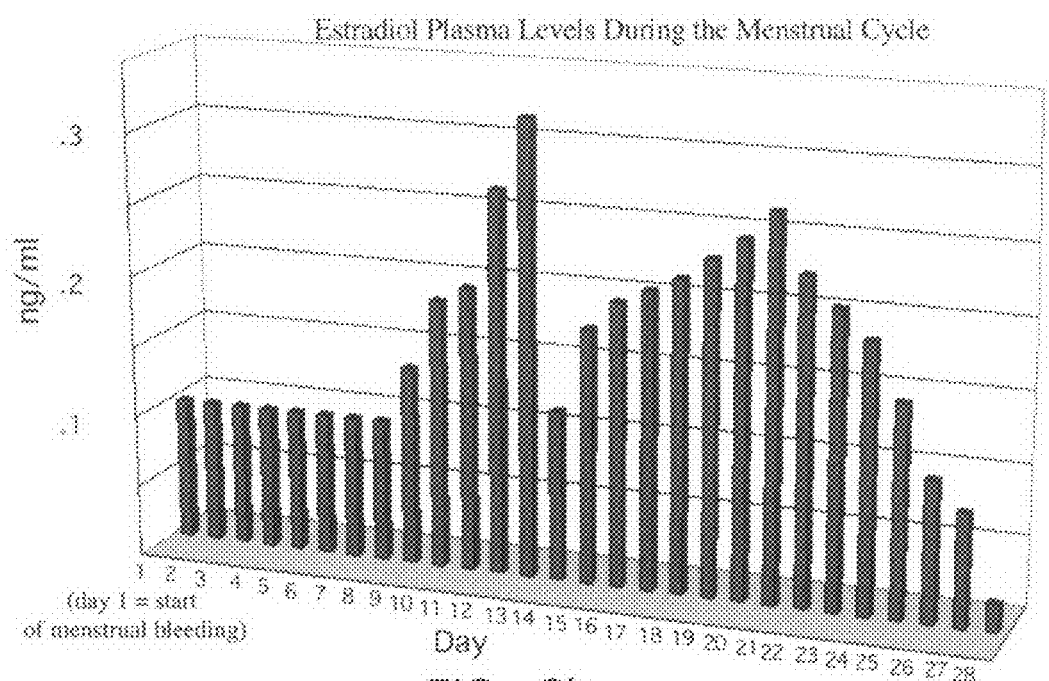

Endocrines, such as estrogen, upregulate transcription of proteins involved in growth control and DNA replication. Estrogen "activates" Cyclin E/CDK2 (FIG. 3) by removing inhibitory protein (P21 and P27) bound to Cyclin E/CDK2, downregulates expression of P21 and P27, and allows progression through the S-Phase. Estrogen and progesterone levels vary throughout the ovulation cycle as shown in FIGS. 6a and 6b, which can in turn result in phase distribution differences from those shown in FIG. 4 (e.g. different S-Phase fractions at any point in time).

Cancer is the accumulation of several independent genetic accidents in growth control pathways that tip the balance in favor of growth. Mutations can occur anywhere along the growth control pathways shown above. Examples include:

Growth Factor Over Expression: Mutations that result in overexpression of growth factors (FIG. 1) by a cell, for which the cell also possesses growth factor receptors, will result in the cell self-stimulating its own perpetual proliferation.

Growth Factor Receptor Overexpression: Mutations that result in overexpression of growth factor receptors (FIG. 1) result in cells that preferentially take up more of the ambient growth factors. Intracellularly, this mimics elevated levels of growth factors, which results in growth and division. HER2 (an EGF receptor) overexpression is found in ~20% of breast cancers, ~30% of non small cell lung cancers, and in ovarian cancers. The EGFR (HER1) receptor overexpression is found in ~50% of glioblastomas (brain cancer), ~15% of breast cancers, ~55% of NSCLC (lung) cancers, ~50% of pancreatic cancers, as well as in head and neck cancers and colon cancer.

RAS Mutations: Mutations that result in the transduction molecule RAS (FIG. 1) being malformed so as to be "always active" result in the transmission of a false "grow" signal to the nucleus. RAS mutations are found in ~25% of cancers.

Rb Deletions: Mutations that result in deficits in Rb protein production (FIG. 3) result in continual activation of the cell cycle. The Rb gene is frequently missing in lung, breast, and bladder cancers.

P53 Mutations: P53 (FIG. 3) is used to inhibit cell division in the presence of genetic damage and in apoptosis induction in severely DNA damaged cells. The absence of a functional P53 gene allows genetically damaged cells to survive and divide, hence allowing cancer causing mutations to accumulate. Certain chemotherapeutics that result in DNA damage rely on P53 pathways to kill cells. Around 50% of cancers have defects in the P53 gene.

Endocrine Independence Endocrine dependence (FIG. 5) is a trait inherent in the cell type from which the cancer arose and is a trait normally retained by the endocrine dependent cancer. However, through time, or through many cycles of DNA damaging chemotherapy, mutations occur that can obviate this secondary control mechanism in these cells.

Regardless of the mutation profile, all cancers have one thing in common. They are a proliferative cell population that is relentlessly growing and dividing (i.e. cell cycle active).

B) Principles of Chemotherapy:

Cancer cells are actively cycling cells and are susceptible to the effects of cell cycle active chemotherapy. However, normal actively cycling cells such as bone marrow, gastrointestinal, skin, and hair cells (the "big 4") cycle at a much faster rate than cancers, and as such are more adversely impacted than the cancer cell population. Additionally, frequent turnover cells include ovaries, testes, thymus, lymph nodes, and spleen. The death of normal actively cycling cells results in systemic toxicity that limits the ability of today's protocols to completely eradicate the cancer cell population.

Many of the existing protocols used today were developed decades ago (referred to as "legacy protocols"). Legacy protocols (e.g. 7 or 21 day administration intervals, given in cycles) were designed primarily to allow for use of maximum tolerated doses and allow for recovery from systemic toxicity. They are not designed to cure cancer.

Legacy Definitions: "Dose limiting toxicity" is the toxicity to normal tissue that limits further dose escalation. Bone marrow toxicity is dose-limiting for most chemotherapeutics. "Maximum tolerated dose" is the dose just below the "dose limiting toxicity".

Figure 7:
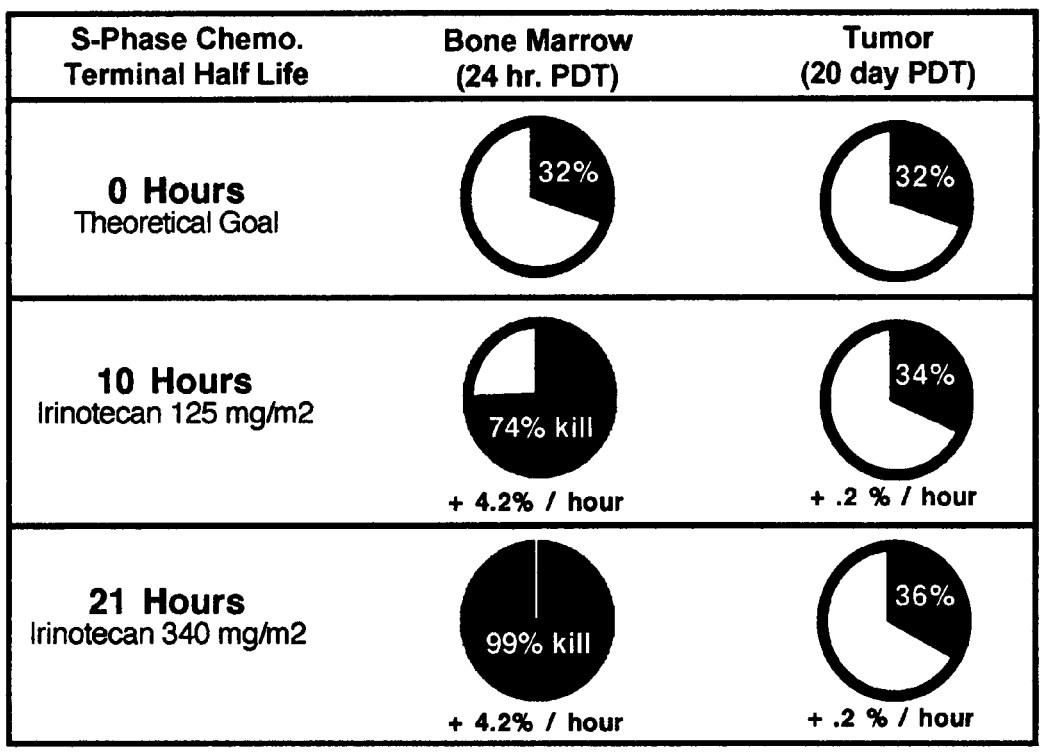
FIG. 7 shows the dose escalation kill tradeoff between normal active cyclers and tumor cells.

From a molecular biology perspective, for a phase specific chemotherapeutic, the maximum tolerated dose equals maximum systemic toxicity, does not necessarily result in an appreciable increase in tumor kill rate (TKR), and does not equal curative result. Using an S-Phase cytotoxic, dose escalation can be used to increase the tumor kill rate as more cells will enter the S-Phase over a longer period of time. However, because bone marrow cycles much faster than a typical tumor, there is a very modest increase in tumor kill rate for a horrific increase in bone marrow kill rate. The example in FIG. 7 shows the tradeoff between bone marrow kill and tumor kill at 3 dose levels for an S-Phase cytotoxic (for a "typical" tumor with a 20 day population division time (PDT)). At a 20 day PDT only 5% of tumor cells enter the S-Phase per day (1 day/20 days) or 0.2% per hour (5%÷24 hours). In contrast, all bone marrow cells would have passed through the S-Phase in one day. The legacy concept of "maximum tolerated dose" is a bad one. The mechanistically correct dose would be the "smallest efficacious dose", defined as the dose that achieves a 100% "in phase kill rate" in the shortest period of time (i.e. to minimize systemic toxicity).

The most valuable tool for constructing high tumor response, theoretically curative protocols, was, and still is, the Skipper log cell kill model. Skipper and coworkers in the 1960's developed the "log cell kill model" for elucidating the effectiveness of a chemotherapeutic protocol in eliminating a tumor mass. An excellent synopsis of this work can be found in Harrison's Principles of Internal Medicine, 14th. edition, pages 527-528. The Skipper log cell kill model is an accurate tool for predicting median survival of legacy protocols, in light of what we now know about tumor kinetics.

Figure 8A:
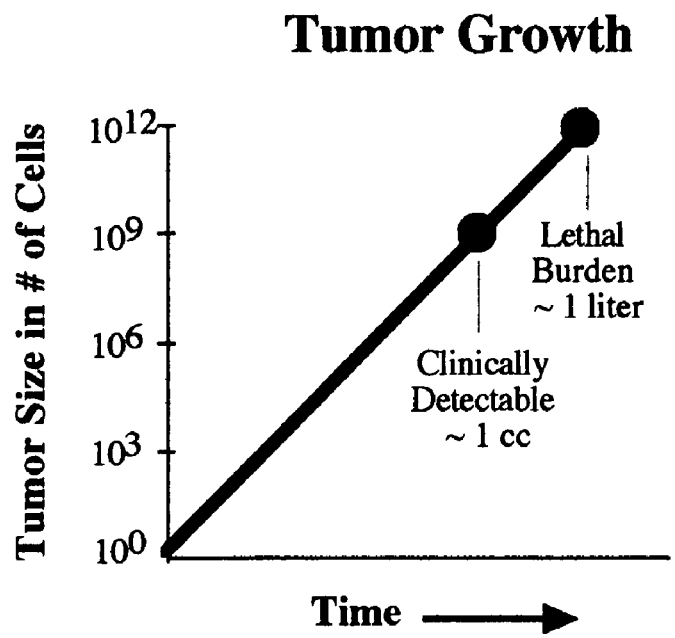
FIGS. 8a and 8b show the textbook Skipper log cell model of tumor growth and kill back.

Skipper identified that tumor growth was logarithmic. From a single aberrant cell, each population division results in doubling of tumor size: i.e. from 1 cell to 2, 4, 8, 16, 32, 64, 128, 256, 512 . . . etc. . . . . Skipper also identified that chemotherapy kills a constant percentage of the tumor. Graphically, this textbook model (per Harrison's 14th edition) is shown in FIGS. 8a and 8b.

Figure 8B:
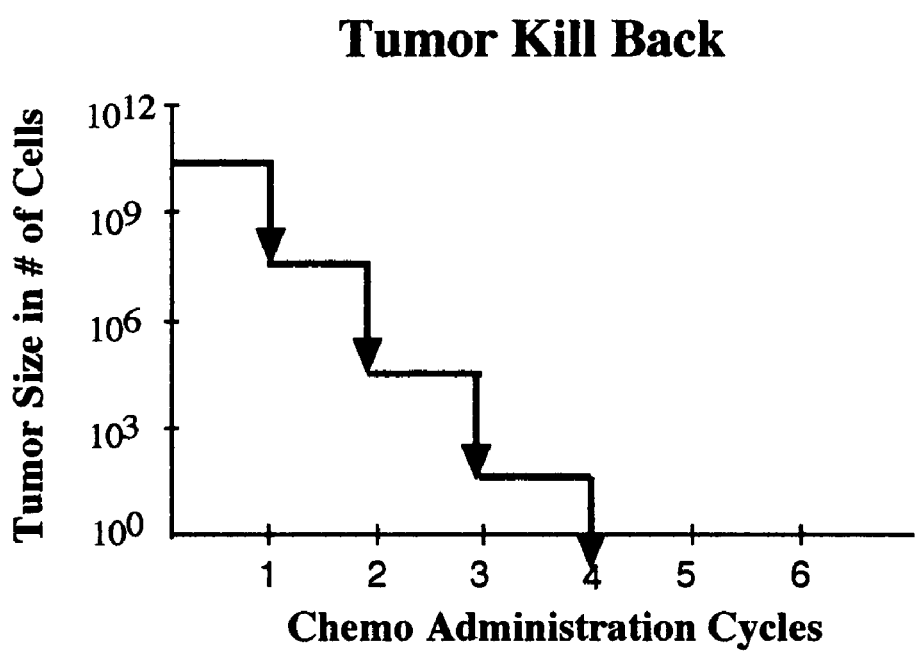

The tumor kill back shown in FIG. 8b is particularly applicable to an S-Phase cytotoxic chemotherapeutic. Roughly 32% of cells are in the S-Phase at any given point in time and can be expected to be killed by an administration of S-Phase cytotoxic. To achieve curative outcome, successive administrations of S-Phase cytotoxic must remain synchronous to the progression of the S-Phase in the cancer. No cancer cells may pass the S-Phase prior to subsequent administrations of the drug and all cancer cells must enter the S-Phase during the efficacy period of one of the administrations of the drug.

A fundamental requirement for curative result under the Skipper log cell kill model is that you must get below the 1 surviving cell number. Just as cancer started from a single aberrant cell, if even a single surviving cell is left alive, the cancer will recur.

Mathematically, for a 10 billion cell tumor, you would need 6 kill cycles of a 99% tumor kill rate chemotherapeutic to achieve this. A 99% tumor kill rate leaves 1% survivors. Accordingly, you must multiply 10 billion by 0.01 six times to get a number less than 1 (i.e. 10,000,000,000×0.01×0.01× 0.01×0.01×0.01×0.01=a number less than 1).

Likewise, for a 10 billion cell tumor, you would need 8 cycles for a 95% tumor kill rate chemotherapeutic (i.e. 10 billion multiplied by 0.05 eight times equals a number <1).

The Skipper log cell kill model can also be used to compute things like normal bone marrow population recovery time. As an example, if the chemotherapeutic kills 99% of bone marrow cells, that leaves 1% survivors. At a 24 hour cell cycle time, the 1% survivors will double to 2%, 4%, 8%, 16%, 32%, 64%, and return to 100% of normal population density on day 7.

Most cytotoxic chemotherapeutics are S-Phase specific and a few M-Phase specific cytotoxics are still used. These chemotherapeutics only kill cells in the susceptible phase (i.e. S-Phase or M-Phase respectively). In a randomly cycling cell population only 32% of the cells are in the S-Phase and 5% are in the M-Phase at any given point in time. Because tumor cell cycle times can average 20+ days, several successive administrations of phase specific chemotherapy, synchronous to the progression of the specific phase (i.e. chemotherapy susceptible phase) in the cancer cell population, are required for one Skipper kill cycle.

For an S-Phase chemotherapeutic with a 99% S-Phase kill rate, 4 successive administrations of the drug, synchronous to the progression of the S-Phase in the cancer cell population, would be required to achieve a 99% tumor kill rate. This assumes no cancer cells have passed through and exited the S-Phase prior to a successive administration of the drug and assumes that all the cells have entered the S-Phase during the course of the 4 administrations. The 4 synchronous administrations of the 99% "in phase kill rate" chemotherapeutic would result in a 99% tumor kill rate and would constitute one Skipper cycle. Six such cycles (24 administrations) would be required to get below the single surviving cell number (i.e. be Skipper compliant).

Likewise, for an M-Phase chemotherapeutic with a 99% "in phase kill rate", 20 synchronous administrations would be required for one Skipper cycle and 120 administrations would be required to get below the single surviving cell number.

The Skipper log cell kill model also requires that there is no "drug vacation" between Skipper cycles, as the tumor cannot be allowed to regrow at any point during the regimen.

None of the legacy protocols used today are Skipper compliant on several levels. Systemic toxicity, particularly using "maximum tolerated dose" concepts, precludes the uninterrupted use of the numerous chemotherapeutic administrations as required by the Skipper log cell kill model.

Furthermore, tumor kinetics preclude the synchronicity of successive administrations of chemotherapy relative to the progression of the phase being targeted by the chemotherapy, under legacy protocols. More specifically, 1) heterogeneity of cell cycle times in a tumor and 2) chemotherapeutic induced acceleration in cell cycle times from tumor size reduction, prevent synchronicity under legacy protocols. To understand the above statement it is necessary to understand Gompertzian tumor growth and its underlying mechanisms of stasis.

Figure 9:
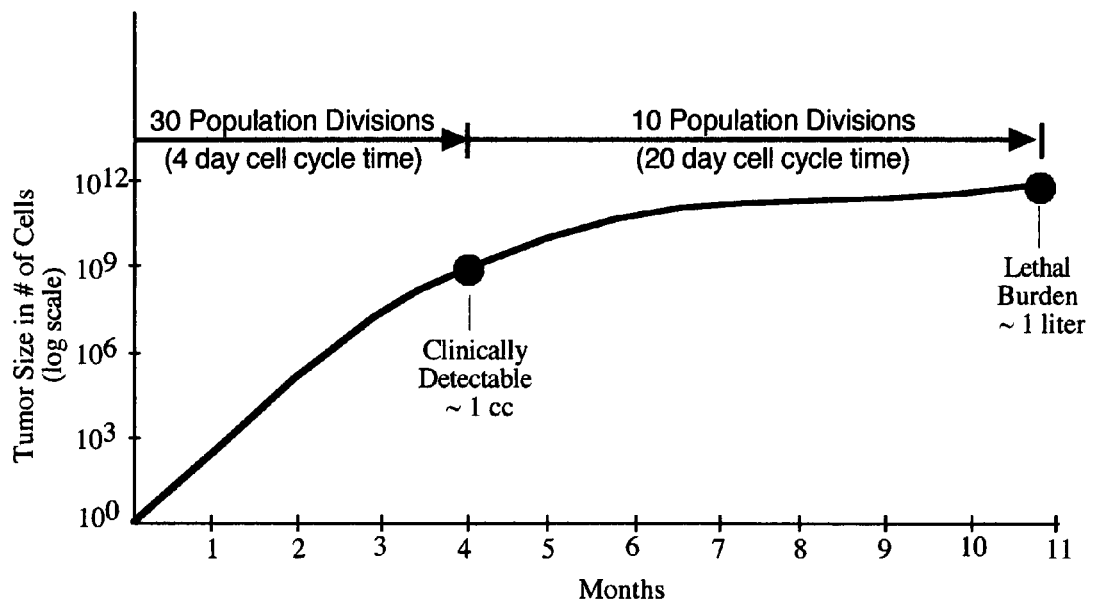
FIG. 9 shows a Gompertzian growth curve for a representative tumor.

C) Gompertzian Tumor Growth:

Tumors follow a Gompertzian growth curve shown in FIG. 9. Mathematically, it takes 30 population divisions from the first aberrant cell to reach a 1 cc (1 billion cell) mass and only 10 more population divisions to reach lethal burden of 1 liter (1 trillion cell) mass. However, the average population division time (and hence the average cell cycle time) slows down significantly past the 1 cc mass.

From a molecular biology perspective, there are several distinct reasons for the slowdown in tumor growth (i.e. the Gompertzian growth curve) and the expectation of heterogeneity of cell cycle times in a tumor (i.e. slower cell cycle times in the dense core, faster cycle times at the periphery).

Figure 10:
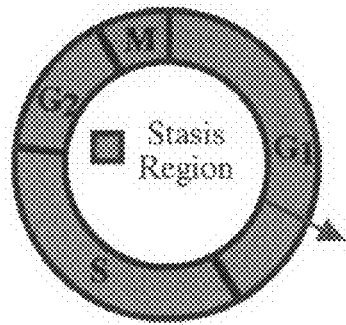
FIG. 10a, 10b, and 10c show the regions in the cell cycle where density dependent stasis points manifest.
Figure 10:
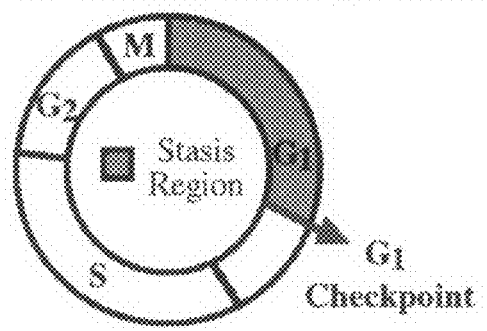
Figure 10:
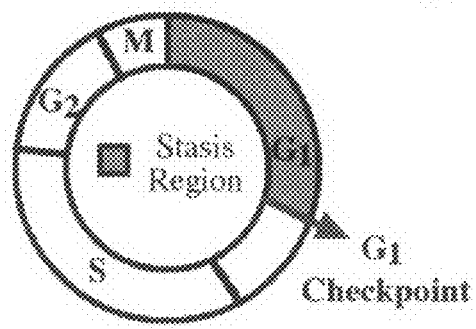

Density Related Stasis 1—Restricted Blood Flow: Increased tumor pressure restricts blood flow, which in turn restricts nutrient and oxygen delivery. A cell needs to double its mass (i.e. proteins, DNA, RNA, lipids, polysaccharides) in order to become two cells. Limiting blood flow limits delivery of the requisite constituents and would slow the progression through the cell cycle. Oxygen is required for glucose metabolism to yield the large amounts of energy rich molecules required to fuel the cell's growth. Likewise, oxygen deprivation would limit the rate of progression through the cell cycle. Mechanistically, nutrient and oxygen deprivation would counteract all cancer mutation profiles, across all phases of the cell cycle as shown in FIG. 10a.

It should also be noted that angiogenesis inhibition can be expected to occur naturally in the denser portions of the tumor. Blood vessel (endothelial) cell growth is stimulated by upregulated vascular endothelial growth factor (VEGF) production in tumors. VEGF uses tyrosine kinase receptor pathways (FIGS. 1-3), which are subject to population density inhibition pathways. As cell density increases, population density pathways tip the balance back toward stasis. Angiogenesis inhibition would further contribute to limiting blood flow in the denser parts of the tumor.

Density Related Stasis 2—Upregulation of Density Dependent Inhibition Pathways: For tumor mutations including overexpressed growth factors, overexpressed growth factor receptors, and transduction and transcription molecule mutations, as tumor density increases, density dependent pathway upregulation can be expected to function antagonistically, tipping the balance toward stasis. As cancer cells reach the peak of the new "population density" inherent in their mutation profile, the antagonistic function of upregulated population density pathways would be expected to result in progressive antagonism in the G-Phase (e.g. P27 in FIG. 3) between the start of the G1 phase and the G1 checkpoint which would result in G-Phase stasis as shown in FIG. 10b. This would manifest as slowed growth and low S-Phase fraction.

Density Related Stasis 3—Ambient Growth Factor Deficits: Tumors that over express growth factor receptors rely on preferential uptake of ambient growth factors to initiate a cell cycle. As a tumor grows, the ratio of ambient growth factors to tumor cells would get progressively unfavorable, leaving many of the overexpressed receptors unbound, which would prevent initiation of a new cell cycle despite the presence of overexpressed receptors. Cells in the dense core of the tumor would have even more restricted access to ambient growth factors. This would result in G-Phase stasis in the region of the cell cycle as shown in FIG. 10c. This would manifest as slowed growth and low S-Phase fraction.

Figure 11:
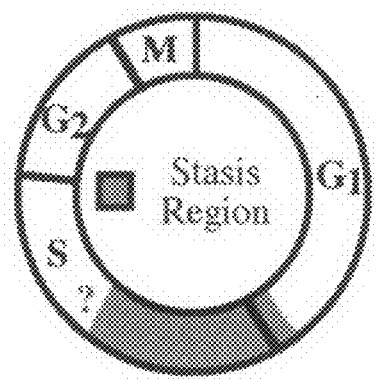
FIGS. 11a and 11b show the regions of the cell cycle where endocrine deficit related stasis and aggregation occurs.
Figure 11:
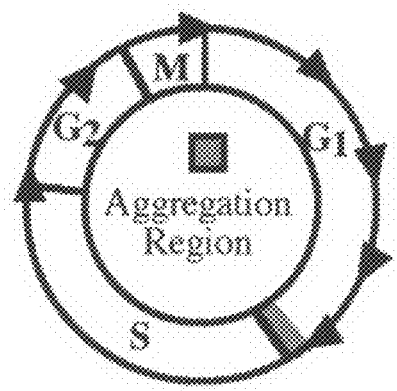

Endocrine Deficit Stasis: Tumors that are endocrine hormone dependent (e.g. estrogen, progesterone, testosterone) would also be subject to endocrine related stasis, both from density related issues and non density related issues. Endocrine hormones are required for entry into and progression through the S-Phase (FIG. 5). Endocrine deficits result in stasis and aggregation as shown in FIGS. 11a and 11b, respectively.

a) Restricted Blood Flow: Endocrine hormones are produced by distant organs and travel through the blood stream to the target tissue. Density related restriction of blood flow would impair delivery of endocrines to endocrine dependent cancer cells. Cells in the dense core of the tumor would have the worst endocrine deficits. Endocrine deficits result in slowed S-Phase progression and progressive aggregation of cells at the G1/S-Phase boundary (FIGS. 11a and 11b).

b) Ovulation Cycle: Endocrine levels such as estrogen and progesterone vary widely throughout the ovulation cycle (shown in FIGS. 6a and 6b). In pre menopausal women, the ovulation cycle includes the formation of tissue masses such as the follicle and corpus luteum that produce spikes in levels of plasma estrogen and progesterone. Post menopausal women do not ovulate and do not have such spikes. It is estimated that around 50% of breast cancers are estrogen dependent and ~40% are progesterone dependent. Nadirs in endocrine levels can be expected to aggregate cells at the G1/S-Phase boundary and spikes would allow entry into and progression through the S-Phase.

c) Chemotherapeutic Ablation of the Ovaries: Chemotherapeutic ablation of the ovaries results in a progressive drop in estrogen and progesterone levels. Shapiro et. al. ("*Ovarian failure after adjuvant chemotherapy* . . . . ", Shapiro C L, Manola J, Leboff M, *Journal of Clinical Oncology*, 2001 Jul. 15; 19(14):3306-11) found that 71% (35 of 49) of pre menopausal women experienced chemotherapy-induced ovarian failure. Ovaries are the primary site of estrogen and progesterone production. Rapidly growing tissue masses such as the follicle and corpus luteum are subject to the cytotoxic effects of chemotherapy.

Mechanistically, endocrine deficits would result in slowed progression through the S-Phase and cells in all other phases of the cell cycle would continue to progress normally until they reached the G1/S-Phase boundary where they would aggregate pending adequate endocrine stimulation as shown in FIGS. 11a and 11b. Aggregation of tumor cells at the G1/S-Phase boundary results in S-Phase depletion (low S-Phase fractions) and M-Phase depletion in the tumor. This prevents response to S-Phase or M-Phase cytotoxic chemotherapy.

D) Why Chemotherapy Fails to Cure Cancer—Gompertzian Related Asynchronicity:

Mechanistically, Gompertzian growth insures today's legacy protocols cannot be used to cure cancer. There are two reasons for this.

1) Heterogeneity of Cell Cycle Times: The density related stasis points discussed above unequivocally imply heterogeneity of cell cycle times in a tumor. Cells in the dense core of a tumor cycle slower than cells at the periphery of the tumor. All of the density related stasis issues presented above would be worst in the dense core of the tumor versus the periphery of the tumor. Blood flow, oxygen delivery, and nutrient delivery would be most impaired in the dense core of the tumor and least impaired at the periphery of the tumor. Density dependent inhibition of cell division pathways would be most upregulated in the dense core and least upregulated at the periphery of the tumor. For cancers over expressing growth factor receptors, the ambient growth factors would be least available (on both an absolute and per cell basis) in the dense core and most available at the periphery of the tumor. For endocrine dependent cancers, endocrine delivery (via blood) would be most impaired in the dense core and least impaired at the periphery. Accordingly, the cell cycle times would be slowest (if not stalled) in the dense core of the tumor. Cell cycle times would be fastest at the periphery. To further complicate matters, cell cycle times could also be expected to vary depending on how far a cancer cell was from a blood vessel (cancer cells stack up to 6 deep from a blood vessel).

Heterogeneity of cell cycle times means inherent asynchronicity of the S-Phase to subsequent administration of S-Phase cytotoxics under legacy protocols (e.g. 7 or 21 day administration intervals). Without synchronicity, curative outcome cannot be expected under the Skipper log cell kill model.

2) Acceleration in Cell Cycle Times from Chemotherapeutic Tumor Depopulation: The reduction of tumor density by chemotherapy would inherently reduce density related stasis mechanisms. This would result in acceleration in cell cycle times and the faster cell cycle times could be expected to be approximately equal to the cell cycle times corresponding to those for a smaller tumor, at a corresponding earlier time on the Gompertzian growth curve. From this faster cycle time, the cells could be expected to progressively slow their cycle times again as they recrowd and as stasis points are reestablished. The acceleration in cell cycle time, however, would leave the accelerated cells asynchronous to the regimen. Without synchronicity, curative outcome cannot be expected under the Skipper log cell kill model.

Clinical Corroboration of Asynchronicity: To corroborate the underlying mechanisms of action (MOAs) as described above, the Irinotecan Phase III clinical trial results for colon cancer, that used a 7 day administration interval (AI) protocol, were used (originally disclosed in U.S. Pat. No. 6,486,146). Irinotecan is an S-Phase cytotoxic (topoisomerase inhibitor) that was administered every 7 days for 4 weeks, followed by 2 weeks off. The study included a group that received only best supportive care (BSC), a group that received 2 cycles of chemotherapy (8 administration), and a group that received 3 cycles of chemotherapy (12 administrations).

With the help of some "rules of thumb", the Skipper log cell kill math can be used to estimate projected average survival time under the proposed "asynchronous" scenario for the 3 patient groups, which could then be compared to actual median survival data from the clinical trials. In an asynchronous environment, only a modest increase in median survival could be expected, and the increase would be directly proportional to the number of administrations of chemotherapy used in the regimen.

Based on the MOA disclosures above, in an asynchronous environment scenario, each administration of S-Phase cytotoxic chemotherapy could be expected to kill the 32% of the tumor cells in the S-Phase but the surviving 68% of cancer cells would continue to cycle at the average population division time (PDT) and keep regrowing the tumor. Accordingly, each administration of chemotherapy would depopulate around 32% of the tumor, and the survivors would repopulate the tumor at the average population division time (PDT).

The average PDT was estimated using 10 population divisions from clinically detectable mass to lethal burden (FIG. 9) applied to the BSC group. The average PDT was estimated from the BSC group as approximately 19 days (i.e. ~190 days survival under BSC÷10 population divisions=19 days/population division).

Cancer regrowth could be calculated using Skipper log cell math as: # of cancer cells at the end of a time period=(starting # of cells)$\times 2^{(\Delta t/PDT)}$; where $\Delta t$ the relevant time period in days, average PDT=19, and advancing the model form a 1 cc mass to the 1 liter (1 trillion cell mass) lethal burden as shown below in TABLE 1 below.

TABLE 1

Skipper Log Cell Kill Model Projection of Progression to Lethal Burden
(Phase III Irinotecan Trials, assuming asynchronicity)

| Chemo. | Day | Week | No Chemo | 8 Admins. | 12 Admins. |
|---|---|---|---|---|---|
| Start | 0 | 0 | 1,000,000,000 | 1,000,000,000 | 1,000,000,000 |
| Chemo | 1 | 0 | 0 | 680,000,000 | 680,000,000 |
| Grow | | 7 | 1 | 1,290,939,198 | 877,838,655 | 877,838,655 |
| Chemo | 2 | 7 | 1 | | 596,930,285 | 596,930,285 |
| Grow | | 14 | 2 | 1,666,524,013 | 770,600,704 | 770,600,704 |
| Chemo | 3 | 14 | 2 | | 524,008,478 | 524,008,478 |
| Grow | | 21 | 3 | 2,151,381,172 | 676,463,085 | 676,463,085 |
| Chemo | 4 | 21 | 3 | | 459,994,898 | 459,994,898 |

TABLE 1-continued

Skipper Log Cell Kill Model Projection of Progression to Lethal Burden
(Phase III Irinotecan Trials, assuming asynchronicity)

| Chemo. | | Day | Week | No Chemo | 8 Admins. | 12 Admins. |
|---|---|---|---|---|---|---|
| Grow | | 28 | 4 | 2,777,302,285 | 593,825,444 | 593,825,444 |
| No Chemo | | 28 | 4 | | | |
| Grow | | 35 | 5 | 3,585,328,385 | 766,592,543 | 766,592,543 |
| No Chemo | | 35 | 5 | | | |
| Grow | | 42 | 6 | 4,628,440,949 | 989,624,362 | 989,624,362 |
| Chemo | 5 | 42 | 6 | | 672,944,566 | 672,944,566 |
| Grow | | 49 | 7 | 5,975,035,847 | 868,730,519 | 868,730,519 |
| Chemo | 6 | 49 | 7 | | 590,736,753 | 590,736,753 |
| Grow | | 56 | 8 | 7,713,407,984 | 762,605,230 | 762,605,230 |
| Chemo | 7 | 56 | 8 | | 518,571,556 | 518,571,556 |
| Grow | | 63 | 9 | 9,957,540,716 | 669,444,349 | 669,444,349 |
| Chemo | 8 | 63 | 9 | | 455,222,157 | 455,222,157 |
| Grow | | 70 | 10 | 12,854,579,625 | 587,664,127 | 587,664,127 |
| NoChemo | | 70 | 10 | | | |
| Grow | | 77 | 11 | 16,594,480,711 | 758,638,656 | 758,638,656 |
| No Chemo | | 77 | 11 | | | |
| Grow | | 84 | 12 | 21,422,465,620 | 979,356,378 | 979,356,378 |
| Chemo | 9 | 84 | 12 | | | 665,962,337 |
| Grow | | 91 | 13 | 27,655,100,585 | 1,264,289,538 | 859,716,886 |
| Chemo | 10 | 91 | 13 | | | 584,607,482 |
| Grow | | 98 | 14 | 35,701,053,368 | 1,632,120,922 | 754,692,714 |
| Chemo | 11 | 98 | 14 | | | 513,191,046 |
| Grow | | 105 | 15 | 46,087,889,201 | 2,106,968,874 | 662,498,437 |
| Chemo | 12 | 105 | 15 | | | 450,498,937 |
| Grow | | 112 | 16 | 59,496,662,721 | 2,719,968,708 | 581,566,736 |
| Grow | | 119 | 17 | 76,806,574,053 | 3,511,314,222 | 750,767,296 |
| Grow | | 126 | 18 | 99,152,617,105 | 4,532,893,166 | 969,194,931 |
| Grow | | 133 | 19 | 128,000,000,000 | 5,851,689,468 | 1,251,171,727 |
| Grow | | 140 | 20 | 165,240,217,337 | 7,554,175,308 | 1,615,186,626 |
| Grow | | 147 | 21 | 213,315,073,638 | 9,751,981,013 | 2,085,107,728 |
| Grow | | 154 | 22 | 275,376,790,072 | 12,589,214,547 | 2,691,747,298 |
| Grow | | 161 | 23 | 355,494,692,509 | 16,251,910,531 | 3,474,882,098 |
| Grow | | 168 | 24 | 458,922,033,223 | 20,980,228,346 | 4,485,861,508 |
| Grow | | 175 | 25 | 592,440,441,489 | 27,084,199,153 | 5,790,974,458 |
| Grow | | 182 | 26 | 764,804,588,367 | 34,964,054,332 | 7,475,795,922 |
| Grow | | 189 | 27 | 987,316,221,893 | 45,136,468,256 | 9,650,797,991 |
| Grow | | 196 | 28 | LETHAL BURDEN | 58,268,436,129 | 12,458,593,418 |
| Grow | | 203 | 29 | | 75,221,008,202 | 16,083,286,595 |
| Grow | | 210 | 30 | | 97,105,747,997 | 20,762,545,097 |
| Grow | | 217 | 31 | | 125,357,616,435 | 26,803,183,315 |
| Grow | | 224 | 32 | | 161,829,060,818 | 34,601,279,971 |
| Grow | | 231 | 33 | | 208,911,477,977 | 44,668,148,613 |
| Grow | | 238 | 34 | | 269,692,015,821 | 57,663,863,945 |
| Grow | | 245 | 35 | | 348,155,994,597 | 74,440,542,271 |
| Grow | | 252 | 36 | | 449,448,220,426 | 96,098,213,934 |
| Grow | | 259 | 37 | | 580,210,325,195 | 124,056,951,221 |
| Grow | | 266 | 38 | | 749,016,251,848 | 160,149,981,109 |
| Grow | | 273 | 39 | | 966,934,439,410 | 206,743,888,164 |
| Grow | | 280 | 40 | | LETHAL BURDEN | 266,893,789,167 |
| Grow | | 287 | 41 | | | 344,543,654,124 |
| Grow | | 294 | 42 | | | 444,784,908,513 |
| Grow | | 301 | 43 | | | 574,190,273,055 |
| Grow | | 308 | 44 | | | 741,244,730,566 |
| Grow | | 315 | 45 | | | 956,901,877,960 |
| Grow | | 322 | 46 | | | LETHAL BURDEN |

Figure 12:
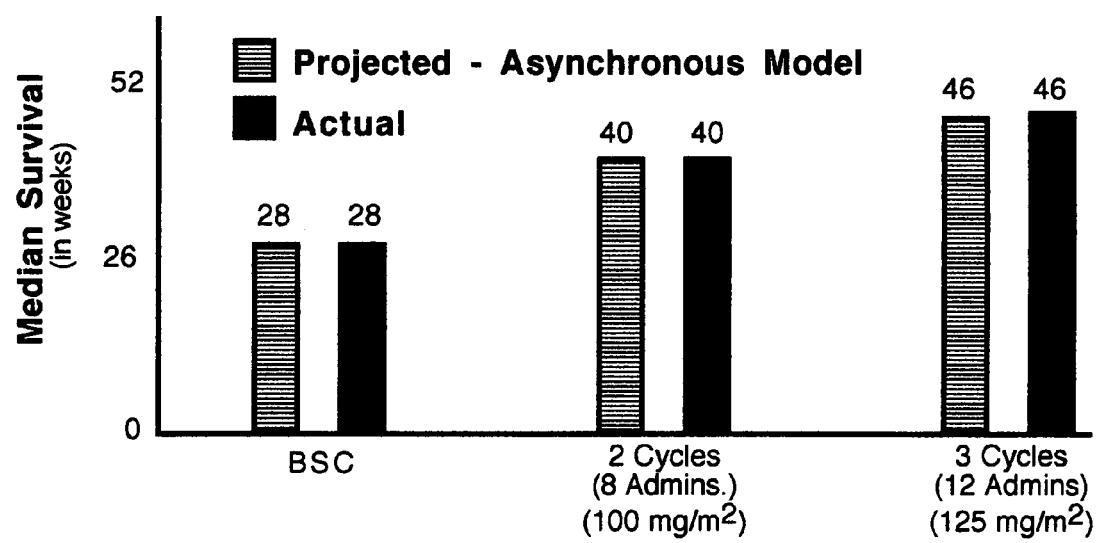
FIG. 12 compares the projected median survival under an asynchronous scenario versus actual median survival.

The comparison of the projected median survival in an asynchronous environment obtained from TABLE 1 is compared to actual median survival from the Phase III clinical trials for the 3 patient groups in FIG. 12. The Skipper projected average survival, using the asynchronous environment scenario, matches the actual observed median survival fairly well as shown in FIG. 12. The data indicates asynchronicity of the legacy protocols. The regimen only delays the cancer's progression to lethal burden by periodically, and asynchronously, killing back about a third of the tumor.

Figure 13:
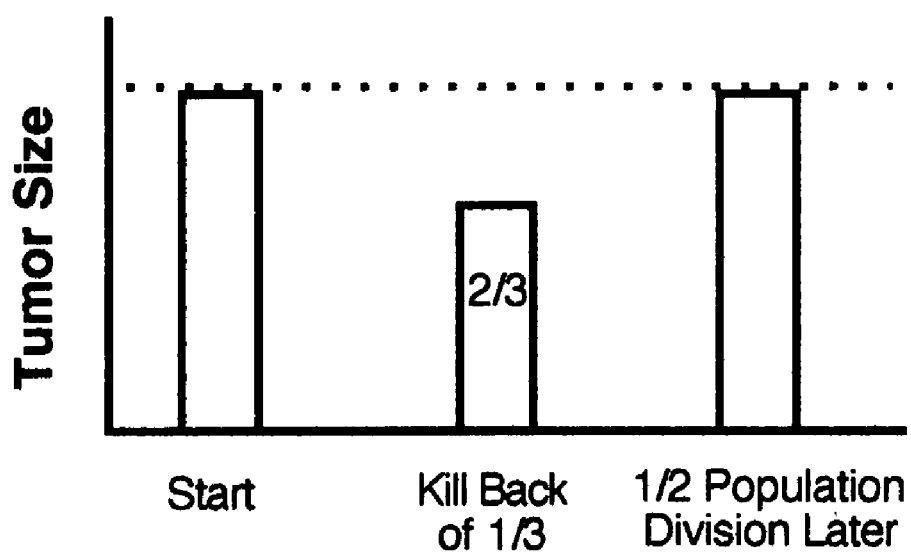
FIG. 13 shows a simplified representation of tumor kill back and regrowth in an asynchronous regimen.

Simplistically, with an asynchronous S-Phase cytotoxic protocol (when AI>0.5 PDT), each administration of S-Phase chemotherapy kills back about at third of the tumor, and the remaining two thirds of the tumor uses up ½ of a population division to restore the tumor to its original size as shown in FIG. 13 (and hence its original place on the timeline of progression to lethal burden). Accordingly, for a 20 day PDT tumor (when AI>10 days), each administration of an S-Phase chemotherapeutic buys you ~10 days of life.

Figure 14:
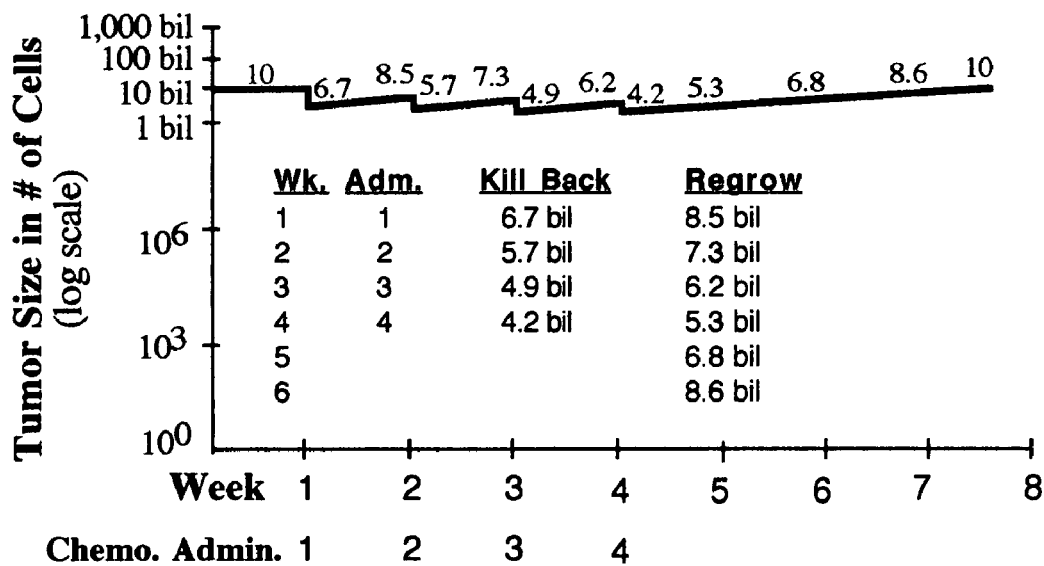
FIG. 14 shows the Zamoyski corrected model of tumor kill back and regrowth for an asynchronous regimen.

Based on both the mechanistic analysis and clinical corroboration presented, the conclusion is that the text book "downward staircase" model of tumor kill back shown in FIG. 8b is wrong. The correct representation, using a typical asynchronous legacy protocol, is shown in FIG. 14. Asynchronous protocols have a "saw tooth" pattern (not staircase) and cannot reach the zero survivor number required for curative result. Surviving cancer cells continue to relentlessly grow at the average PDT until lethal burden is reached. Administration of an S-Phase cytotoxic kills roughly one third of cancer cells (i.e. the cells that were in the S-Phase), however the kill back over 4 administrations is not cumulative as envisioned by the textbook "stair case" model in FIG. 8a but instead can be viewed as 4 relatively independent events that only serve to modestly delay the progression to lethal burden as shown in FIG. 14.

Based on the information above, we can also analyze other currently used S-Phase protocols to understand their failure to achieve appreciable curative outcome.

Legacy protocols that use 7 or 21 day administration intervals (AIs) cannot achieve curative outcome as outlined above and summarized in FIG. 14. Furthermore, they are self defeating by definition, as if they could reduce a tumor in size to less than 1 cc, the elimination of all density related stasis points would result in all tumor cells cycling at the 4 day rate (=1.3 day S-Phase transit time). Only a daily S-Phase cytotoxic AI would be synchronous at that point.

Today's protocols also use lower doses administered daily for 3-5 days and very low doses administered daily for up to 21 days. Neither of these regimens can be expected to yield curative result based on the underlying MOA and math disclosed.

The 20 day PDT (population division time) for the colon cancer example presented is an average. Mechanistically, cells at the periphery can have a cell cycle time as short as 4 days and cell in the dense core can have a cell cycle time of 40 days or more (if not in stasis completely). Low dose, daily regimens administered for up to 5 days can only be expected to remain synchronous to the cells at the outermost periphery of the tumor which are cycling at the 4 day rate. With a 32% S-Phase fraction, the amount of time these outermost cells would spend in the S-Phase would be 1.3 days (i.e. 4 days× 0.32=1.28) which puts their S-Phase synchronous to the daily administration. However, cells cycling at the average 20 day rate or even a 40 day rate at the core would not only be asynchronous to the regimen but most of them would have never even entered the S-Phase during the 5 days. Accordingly, a 4 day, daily administration regimen would be good for killing the tumor periphery to define a clean margin prior to surgery, however it cannot be expected to yield curative outcome as a stand alone treatment.

Likewise, prior art very low dose daily administrations for 21 days will not kill all of the slower cycling cells at the dense core (i.e. the 40 day cycle cells). Furthermore, ultra low dose regimens also have questions about their ability to achieve the 100% in phase kill rates (also a requirement for curative outcome) of their regular dose counter parts. Simply put, if the very low doses had a 100% in phase kill rate, there would be no reason to ever use the regular dose levels.

It should be noted that from an MOA (mechanism of action) perspective, asynchronous regimens can result in curative outcome in special situations. As an example, roughly 10% of cancers do not display telomerase upregulation and accordingly are subject to cell senescence. A typical cell (non stem, non malignant) has between 40-60 cell cycles before telomere reduction results in cell senescence. It takes 40 cycles to reach average lethal burden. Killing back cancer cells forces surviving cancer cells to use more cell cycles to achieve lethal burden. Depending on how many cell cycles were used up before the cell became cancerous, and if enough cell cycles are used up by asynchronous chemotherapy, cancers that do not have upregulated telomerase may eventually go senescent and never reach lethal burden. As another example, a very weak mutation profile that results in the "fastest cell cycle" time being fairly slow and coincidentally synchronous with a 7 day administration interval would also be cured if enough administrations were given.

However, the low survival rates for late stage cancers (i.e. 1% for lung cancer, 2% for pancreatic cancer, 5% for colon cancer), whose primary treatment course is chemotherapy, clearly indicates that the legacy protocols in use today are not curative in the vast majority of cases.

2) Skipper Compliant, Tumor Specific, Cell Cycle Synchronous Protocols

Having covered why legacy protocols fail to cure cancer, we can now construct protocols to avoid these pitfalls. The enormous potential therapeutic benefit of synchronous protocols had not escaped researchers and spawned many studies in the 1970's and 1980's, however without any success. The failures have gone a long way to "poison the well" for future research in this area. Accordingly, the section below outlines why the prior art attempts failed and how to fix them.

This section outlines the requirements for Skipper compliant, tumor specific, cell cycle synchronous protocols and also reviews prior art pioneering studies to demonstrate the importance of adherence to the principles of tumor specific, synchronous chemotherapy as established in this section. The most prevalent failure in prior art pioneering protocols relates to lack of tumor specificity. Without tumor specificity, fast cycling cells, such as bone marrow cells, are preferentially aggregated over the much slower cycling tumor and the result is high hematologic/systemic toxicity and low tumor response. In contrast, tumor specific aggregation would result in high tumor toxicity and low hematologic/systemic toxicity.

Because this section pioneers new principles, a few definitions are in order.

Cell Cycle Synchronous Chemotherapy—Defined as protocols where successive administrations of phase specific cytotoxic chemotherapeutic are synchronous relative to the progression or aggregation of cells in the susceptible phase (i.e. the phase in which the chemotherapeutic exerts its cytotoxic effect) in a hyperproliferative cell population targeted for ablation.

Synchronizing agent(s)—Defined as a compound or combination of compounds that are used to aggregate cells in a desired region(s) of the cell cycle, and when possible also include a compound(s) which then releases the aggregated cells, at an opportunistic time relative to the administration of a phase specific cytotoxic chemotherapeutic.

Cytostatic—A compound that induces stasis (i.e. cellular arrest) during the cell cycle.

Anti-Cytostatic—A compound that reverses the action of a cytostatic, allowing a cell to progress through the cell cycle.

Accelerant—A compound that accelerates the progression of a cell through a given phase(s) or region(s) of the cell cycle.

Phase enrichment—increasing the number or proportion of cells in a given phase of the cell cycle.

Phase depletion—decreasing the number or proportion of cells in a given phase of the cell cycle.

Aggregation—Progressively increasing the number or proportion of cells in a given phase or region of the cell cycle, over a period of time.

One Cycle of Chemotherapy—For an S-Phase cytotoxic: Defined as several administrations of chemotherapy, given sequentially, so that the "in phase kill rate" equals the "tumor kill rate". For a tumor with uniform cell cycle times, a minimum of 4 administrations are required, for a larger tumor with non uniform cell cycle times, 8 or more administrations may be required.

Skipper Compliant—For an S-Phase cytotoxic: Several cycles of chemotherapy, administered sequentially and uninterrupted, so that the less than one surviving cell number is reached. Mathematically: (tumor size in # of cells)×(1−tumor kill rate)$^n$<1, where n=number of cycles of chemotherapy (previously disclosed under principles of chemotherapy)

There are several criteria which must be met in order to insure high tumor response, substantial increases in median survival rates, and to be Skipper compliant. They are:

Criteria 1) Cancer Specific Synchronization: The synchronization must be preferential to cancer.

Criteria 2) Gompertzian/Stasis Sensitive: Must remove stasis points and prevent their reestablishment.

Criteria 3) Skipper Compliant Regimen: Cycles must be synchronous and without breaks between cycles.

Criteria 4) Cytostatic/Cytotoxic Compatibility: The synchronizing method must be synergistic with the cytotoxic.

Criteria 5) Endocrine Stasis Sensitive: Endocrine dependence must be factored into regimen.

Criteria 1): Cancer Specific Synchronization

An absolute requirement of synchronization (i.e. phase enrichment, phase aggregation etc. . . . ) is that it is cancer specific, or alternatively made tumor specific via the protocol. The synchronizing agent(s) must aggregate the cancer cells and must not aggregate active cyclers such as bone marrow cells or other crucial normal cell populations. If the synchronizing agent is not cancer specific, it will result in preferentially high systemic toxicity with little difference in tumor response (because normal active cyclers have much faster cell cycle times than tumor cells).

Examples of bad pioneering protocol choices of phase enriching agents include

Vincristine: M-Phase microtubule assembly inhibitor
Bleomycin: G2 and M-Phase DNA breakage via free radical generation
Hydroxyurea: S-Phase antimetabolite
Ara-C (cytarabine): S-Phase pyrimidine analog
DAG (dianhydrogalactitol): S-Phase alkylating agent, cross links DNA
Methionase: Late S/G2 arrest via methionine depletion The above are not cancer specific. They will result in preferentially high systemic toxicity with little difference in tumor response.

As an example, for an S-Phase cytostatic: At a one day cell cycle time for bone marrow cells, 32% of the cells will be in the S-Phase at any given point in time plus 4% of the remaining cells will be entering the S-Phase per hour (i.e. 1 hour÷24 hours). Accordingly, within 16 hours, 100% of the bone marrow cells would have been in, or passed through, the S-Phase and have been aggregated.

Figure 15:
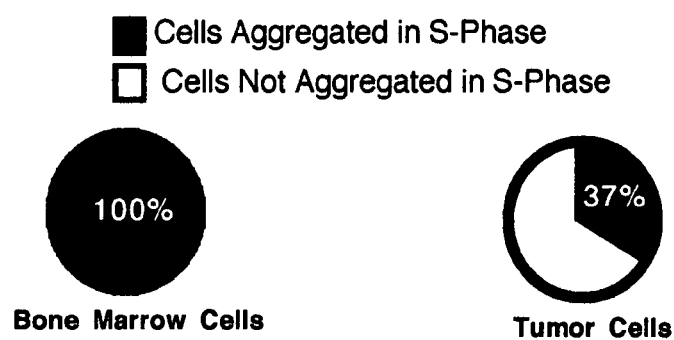
FIG. 15 shows the tradeoff between bone marrow cell and tumor cell aggregation using non tumor specific aggregation.

In contrast, a tumor that takes on average 20 days to progress through the cell cycle will only have 5% (i.e. 1 day÷20 days) of new cell entering the S-Phase per day, or only 0.2% per hour. It would take at least 14 days to aggregate the majority of the tumor cells (assuming a best case scenario that the tumor had a 32% S-Phase fraction to start with). Over the course of one day, aggregation using a non tumor specific S-Phase aggregator, would result in preferential bone marrow aggregation with modest tumor aggregation as shown in FIG. 15.

Likewise, other non tumor specific cytostatics, such as non tumor specific cyclin or CDK blockers, non tumor specific kinase inhibitors, etc. . . . hold exceptional potential for being added to the list of bad choices for aggregating agents in the future.

Criteria 2) Gompertzian/Stasis Sensitive:

The first goal of a synchronous regimen is elimination of all stasis points, other than the stasis point being used to aggregate the cells. This inherently includes preventing reestablishment of density related stasis points over the course of a cycle and over the course of a regimen (i.e. progressively reduce tumor size and also prevent regrowth). The goal over the first few cycles is to depopulate the tumor to the point where all cells in the tumor are cycling at the fastest possible rate inherent in their genetic mutation profile (i.e. elimination of all density related stasis points). Density related stasis points preclude complete aggregation as cells arrest prior to reaching the aggregation point. Complete aggregation cannot be achieved until all other stasis points (i.e. other than the one being used to aggregate the cells) are removed.

Figure 16:
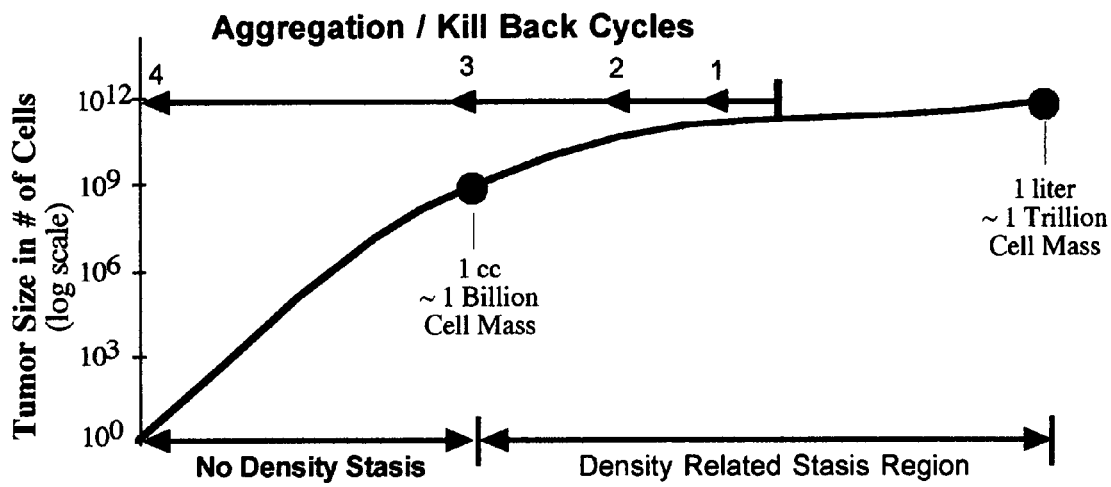
FIGS. 16a and 16b show the principle of Gompertzian/Stasis sensitive, progressive tumor reduction.
Figure 16:
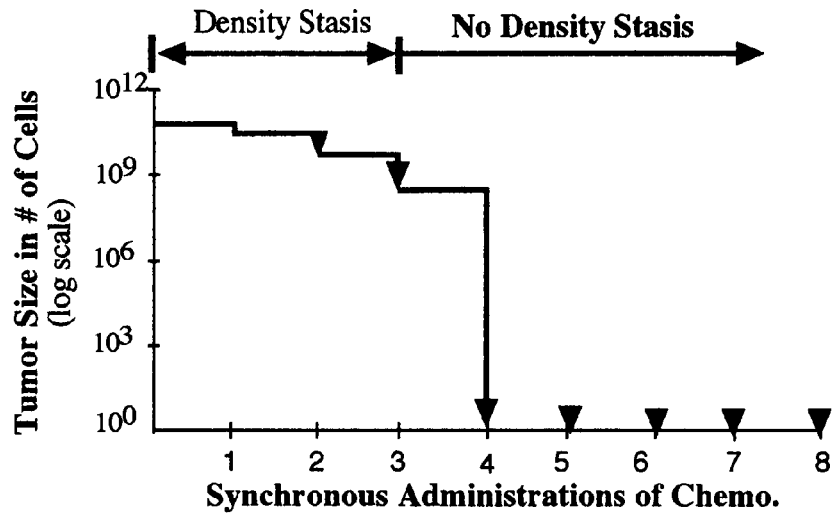

The process is effectively moving back from right to left on the Gompertzian growth curve of as shown in FIG. 16a, to the linear, pre 1 cc, part of the curve. The linear part of the growth curve has a constant slope, indicating the uniform, "fastest cell cycle time" that existed under optimal conditions prior to crowding and the establishment of density related stasis points. Complete aggregation, and hence extremely high tumor kill back, cannot be predictably achieved until all other stasis points are progressively removed as shown in FIG. 16a.

Accordingly, the progressive elimination of density related stasis points, and hence the progressively better aggregation and kill back would result in a uneven staircase pattern as shown in FIG. 16b.

Since all of the density related stasis points result in G-Phase arrest, low S-Phase fractions can be expected, and they can be expected to be inversely proportional to tumor density. It is not unusual for tumors to have as little as 10%-15% of cells in the S-Phase. Accordingly, the first few cycles can result in quite small tumor response. Furthermore, even if the tumor has a normal 32% S-Phase distribution, and all of the S-Phase cells are killed with the first administration of S-Phase cytotoxic, the 23% of cells that were in the G2 and M phases will become two cells shortly (in 5 days for a 20 day cycle time) and the 23% additional cells offsets part the 32% S-Phase kill off. Accordingly, the first administration can mechanistically be expected to have the most modest tumor kill back, with the kill back progressively increasing over the course of the cycle, and the true power of the regimen not manifesting until all density related stasis points are removed as shown by the progressive staircase pattern in FIG. 16b.

Elimination of density related stasis points (in a non endocrine dependent tumor) would result in a uniform tumor cell cycle time. A uniformly cycling tumor is easy to kill.

A synchronous regimen, using synchronizing agents and phase specific cytotoxics, may be used to complete the eradication. Aggregation times may be shortened accordingly.

Alternatively, a uniformly cycling tumor can also be killed with a straight cytotoxic regimen, provided the cell cycle time is appreciably different than the 1 day cycle time of normal active cycling cells. A regimen that is "synchronous" to the cancer cell cycle time and "asynchronous" to the bone marrow cell cycle time can be used. As an example, using a 1-2 hour terminal half life S-Phase cytotoxic and assuming a 4 day "fastest cancer cell cycle time" means the cancer cells will spend 13 days in the S-Phase and 4 daily administration of an S-Phase cytotoxic will constitute one true "staircase" Skipper cycle (FIG. 8b). The 1 day bone marrow cycle time translates into ~8 hours in the S-Phase, which means the daily administration of the S-Phase cytotoxic is "asynchronous" to the bone marrow cell population and would result in the "saw tooth" pattern of FIG. 14 from which the population readily recovers.

Criteria 3) Skipper Compliant Regimen

Aggregation and kill back is a continual, ongoing process, throughout the regimen. No "breaks" or "drug vacations" are allowed between cycles. Uninterrupted aggregation and kill back is consistent with the true "uneven staircase" pattern of FIG. 16b. "Breaks" between cycles in a synchronous regimens allow for reestablishment of stasis points, which perpetually puts the regimen back at the early cycles shown in FIG. 16b. "Breaks" between cycles result in asynchronicity and hence the discrete, relatively independent kill back consistent with the failed "saw tooth" pattern shown in FIG. 14.

The number of cycles required for complete eradication are computed, post elimination of density related stasis points (e.g. cycle 4 in FIG. 16b), using the Skipper log cell kill model as previously disclosed.

Criteria 4) Cytostatic/Cytotoxic Compatibility

Phase enrichment is a term used by many pioneering protocols. Phase enrichment was typically defined as increasing the fraction (proportion) of cells in a given phase of the cell cycle, typically the S-Phase. However, increasing the S-Phase fraction does not automatically mean the action of an S-Phase cytotoxic will be enhanced.

As an example, slowing down the rate of DNA replication in the S-Phase would increase the amount of time it took the cell to progress through the S-Phase (and hence boost the S-Phase fraction). However, this would be antagonistic to the function of certain S-Phase cytotoxics, such as topoisomerase inhibitors, that rely on the torsional strain acquired during DNA replication for their cytotoxic effect. Mechanistically, reducing the rate of DNA replication two fold would double the "S-Phase fraction" however it would cut in half the amount of torsional strain and DNA damage inflicted by the topoisomerase inhibitor. In contrast, accelerating the DNA replication rate two fold would result in twice the amount of unrelieved torsional strain and DNA damage during the efficacy period of the topoisomerase inhibitor, even though it would result in "phase depletion" rather than "phase enrichment".

Criteria 5) Endocrine Stasis Sensitive

Endocrine dependence must be factored into a regimen for endocrine dependent cancers, as this secondary cell cycle control pathway will prevent any regimen from working as envisioned if not factored into the regimen. The variability in estrogen and progesterone levels during the ovulation cycle alone can result in undesirable stasis at inappropriate times in the regimen. Post menopausal women will have natural endocrine deficit stasis that would prevent synchronicity.

Endocrine Hormone Based Synchronization Methods

Endocrine dependence, such as estrogen, progesterone, or testosterone dependence is an exceptionally fortunate occurrence for cancer specific, cell cycle synchronous regimens.

Administration of endocrines allows for precise release of aggregated cells into the S-Phase, at an opportunistic time relative to the administration of an S-Phase cytotoxic. Endocrine downregulation or blocking allows for enhanced G1/S-Phase boundary aggregation. Many drugs and methods exist for reducing or increasing endocrine hormone levels.

Since bone marrow and other normal active cyclers do not possess these endocrine receptors, they are not synchronized to administrations of S-Phase cytotoxics. To be synchronized a cell must 1) posses the specific endocrine receptor and 2) be actively cycling—which makes the regimen fairly specific (and synchronous) to the cancer cell population.

Prior art has also attempted to use endocrine synchronization and failed. This has also gone a long way to "poison the well" for newer protocols from being tried. However, when viewed in light of the "Principles of Tumor Specific, Cell Cycle Synchronous Chemotherapy" disclosed above by applicant, the reason for failure emerge and corrected protocols are provided.

Lippman et. al. ("*A Randomized Attempt to Increase Efficacy of Cytotoxic Chemotherapy in Metastatic Breast Cancer by Hormonal Synchronization*", Mark E. Lippman, Jane Cassidy, Margaret Wesley, and Robert C. Young, *Journal of Oncology*, Vol. 2, No. 1, January, 1984) conducted a study on 110 patients using a stand alone chemotherapeutic regimen or the same regimen with estrogen function downregulation followed by estrogen upregulation. Lippman concluded that "No difference in any response parameter was seen between these two 5-FU/MTX schedules." Applicant identified the deficiencies in the Lippman protocols and in U.S. Pat. No. 6,486,146 applicant took a completely different approach by using only endocrine upregulation (claims 1-4) and an exactly opposite approach to Lippman by reversing the order of administration to estrogen upregulation followed by estrogen downregulation (claims 5-8). More specifically, the Lippman's protocols can be summarized as follows:

TABLE 2

The Lippman Protocols

| Day | Drug | Class | Control (CAMF) | Study (CAMFTP) |
|---|---|---|---|---|
| 1 | C—cyclophosphamide | Non-Phase Specific | ✓ | ✓ |
| 1 | A—doxorubicin | S-Phase Cytotoxic | ✓ | ✓ |
| 2-6 | T—Tamoxifen | G1/S-Phase Cytostatic | | ✓ |
| 7 | P—Premarin (estrogen) | Anti-Cytostatic | | ✓ |
| 8 | M—methotrexate | S-Phase Cytotoxic | ✓ | ✓ |
| 8 or 9 | F—fluorouracil (5-FU) | S-Phase Cytotoxic | ✓ | ✓ |
| 10-21 | No Drug | "asynchronicity & stasis re-establishment" | ✓ | ✓ |

The Lippman protocol is a mechanistically meaningless "aggregation and release" protocol. The brief "aggregation of cells" on days 2-6 of a 21 day cycle is meaningless, particularly in context of S-Phase chemotherapy on days 1 and 8, because the cells in the control group would have progressed on their own to the same place in the cell cycle. Only the "release" on day 7 was the relevant, and extremely significant, as discussed below in the: "Endocrine Release—Extremely Significant" section.

The deficiencies in the Lippman protocols, under Principles of Synchronous Chemotherapy, are as follows:

Tumor Specificity Deficiency—Only 15% of the patients in the CAMFTP group were estrogen receptor positive, 42% were estrogen receptor negative, and the status of the remainder was not known (Lippman et. al. study, Table 2. *Distribution of Prognostic Factors by Treatment Group*). Estrogen modulated aggregation and synchronization will only work on estrogen dependent cancers.

Not A Synchronous Regimen—Synchronous regimens require continues, uninterrupted aggregation and synchronization relative to successive administrations of phase specific cytotoxics over every cycle and throughout the course of the entire regimen. The brief "aggregation of cells" on days 2-7 of a 21 day cycle could only be described as a transiently synchronous regimen (and without any advantage relative to the control group).

Gompertzian/Stasis Insensitive—Breast cancers take ~30 days to complete the cell cycle (see below) and as such the 2 administration of S-Phase cytotoxics on days 1 and 8 of a 21 day cycle do not even constitute one legitimate cycle of chemotherapy (see definition above). Continuos, uninterrupted aggregation and kill back over the course of a cycle of chemotherapy is required to insure progressive tumor reduction, otherwise tumor regrowth occurs, density dependent stasis points are reestablished, and the downward staircase pattern of FIG. 16b cannot be achieved. For the Lippman protocols, only the first two administrations in FIG. 16b are periodically repeated.

Not Skipper Compliant Regimen—The two week "off" period throughout the regimen results in the traditional asynchronicity prior to the start of each cycle (i.e. the "saw tooth" pattern of FIG. 14).

Endocrine (Progesterone) Stasis Insensitivity—The Lippman protocols did not factor in progesterone dependence and potential progesterone deficit related stasis.

Cytostatic/Cytotoxic Incompatibility—Estrogen was administered during the efficacy period of the Tamoxifen. Tamoxifen competes with estrogen for binding to estrogen receptors. Tamoxifen has a plasma concentration half life of 5-7 days and its major functional metabolite has a half life of 14 days (*Physician's Desk Reference*, 54th. ed., p. 547). Discontinuation of tamoxifen only one day prior to administration of estrogen, and 2 days prior to the S-Phase Cytotoxic, implies a potential level of continued cytostatic activity, which would have been antagonistic to the function of the estrogen and hence the S-Phase cytotoxic.

Endocrine Release—Extremely Significant—The brief aggregation of cells on days 2-6 by tamoxifen was relatively meaningless, in context of an S-Phase cytotoxic kill back on days 1 and 8 and in light of an approximate 30 day breast cancer PDT. Only the estrogen (premarin) administration on day 7 was relevant. After killing cells in the S-Phase on day 1, cells in the G-Phase would have continued to progress through the cell cycle and either aggregated at the G1/S-Phase boundary if an endogenous estrogen deficit existed or would have progressed into the S-Phase if there was no estrogen deficit (where most of them would have been killed by the administration of S-Phase cytotoxic on day 8).

Mechanistically, the overwhelming number of patients (80+%) in the study group would have had estrogen deficits naturally, making the tamoxifen aggregation unnecessary (i.e. 70% of the women in the study group were post menopausal (per Table 2. of the Lippman et. al. study) plus some percentage of the remaining women would have natural menstrual cycle related nadirs). Factoring in Shapiro's 71% chemotherapy induced ovarian failure rate, the number of estrogen deficient women would have progressively risen to more than 90% over the course of the regimen.

Accordingly, tamoxifen was not needed to aggregate cells—the cells would have naturally aggregated in the same place because of the estrogen deficit. The patients did not need the tamoxifen, they did however need the premarin to release their natural G1/S-Phase boundary arrest prior to the administration of the S-Phase cytotoxic.

The Lippman protocols inadvertently provide clinical corroboration for the power of using endocrine upregulation to enhance the efficacy of chemotherapy (i.e. 2 month increase in median survival—in a group not even selected based on estrogen dependence, despite the administration of estrogen during the efficacy period of the tamoxifen, and using a regimen that violated basically every rule under both principles of chemotherapy and principles of cell cycle synchronous chemotherapy.)

Applicant's protocols for estrogen and/or progesterone (i.e. endocrine) dependent breast cancer are covered under U.S. Pat. No. 6,486,146 (hereinafter referred to as the '146 protocols). They take an completely different approach to prior art legacy protocols by using only endocrine upregulation prior to an S-Phase cytotoxic (claims 1-4) and an exactly opposite approach to Lippman by reversing the order of administration to estrogen upregulation followed by estrogen downregulation (claims 5-8) as well as continuing the aggregation for the entire duration of the cycle.

The first set of claims of '146 (i.e. 1-4) address the fatal flaw in all legacy protocols used for endocrine dependent breast cancers: ESTROGEN OR PROGESTERONE DEFICIT RELATED STASIS MUST BE REMOVED FOR ANY S—PHASE CYTOTOXIC PROTOCOL TO WORK PROPERLY. Endocrine deficit related stasis is to be expected in post menopausal women, in women with chemotherapeutic or other ablation of the ovaries, and from normal ovulation cycle related nadirs in pre menopausal women. The administration of estrogen or progesterone insures efficacy of S-Phase chemotherapy and mathematical integrity of protocols. To this day, administration of estrogen or progesterone, prior to S-Phase cytotoxics, is not done.

Figure 17A:
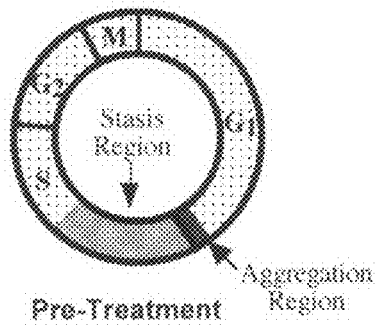
FIGS. 17a through 17f show cancer cell distribution during administrations of drugs under protocols of U.S. Pat. No. 6,486,146.
Figure 17B:
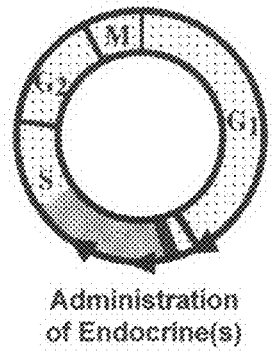
Figure 17C:
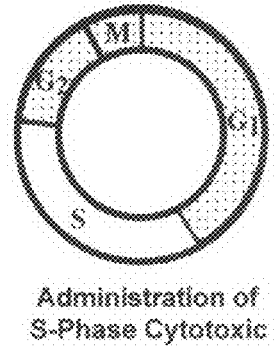

For endocrine dependent cancers, low levels of endocrines such as estrogen or progesterone result in slowed progression through the S-Phase and S-Phase depletion via aggregation of cancer cells at the G1/S-Phase boundary (FIGS. 11a and 11b). Diagrammatically, the phase distribution of cancer cells during the first administration cycle of the '146 protocols (U.S. Pat. No. 6,486,146, Claims 1-4) is shown in FIG. 17a, 17b and 17c. The endocrine administration selectively sweeps any aggregated cancer cells (FIG. 17a) into the S-Phase (FIG. 17b) plus accelerate the progression rate of cancer cells through the S-Phase. Mechanistically, this provides a dual action for improved tumor response. First, this results in a much greater number of cells being in the S-Phase, which in turn are killed by the S-Phase cytotoxic. Second, the accelerated S-Phase progression (and hence accelerated DNA replication rate) mechanistically enhances the efficacy (kill rate) of many S-Phase cytotoxics that target DNA replication pathways (e.g. topoisomerase inhibitors). The administration of the S-Phase cytotoxic (17c) kills the aggregated cells, which are now in the S-Phase.

Figure 17D:
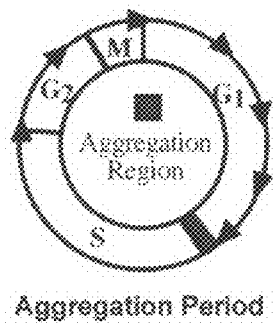
Figure 17E:
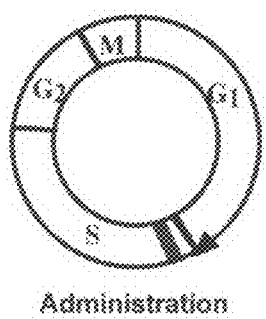
Figure 17F:
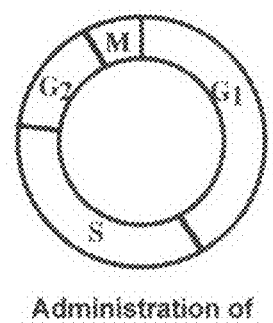

The time between administration serves to aggregate cells at the G1/S-Phase boundary (naturally in patients with natural endocrine deficits) as shown if FIG. 17d, and successive administrations of endocrines release the aggregated cells into the S-Phase (FIG. 17e) where they are killed by the S-Phase cytotoxic as shown in FIG. 17f.

The second set of '146 protocols (U.S. Pat. No. 6,486,146, Claims 5-8) further enhances the reliability of the first set of protocols by adding endocrine downregulation to enhance/insure aggregation (of FIG. 17d). Successive cycles of '146 are repeated in accordance with principles of cell cycle synchronous chemotherapy as outlined above, versus the violation of virtually every principle by the Lippman protocols.

The importance of the '146 protocols is that, for regimens of present invention that use receptor blockers with S-Phase cytotoxics, when treating endocrine dependent cancers, endocrine dependent stasis must be removed to insure S-Phase cytotoxic function and synchronicity (i.e. '146 protocols must be integrated into protocols of present invention).

Angiogenesis Inhibitors and '146 Protocols and/or protocols of present invention: Protocols of '146 and present invention can incorporate use of angiogenesis inhibitors to protect tumor vasculature from the cytotoxic effects of chemotherapy in order to prevent chemotherapeutic ablation of tumor vasculature in order to facilitate "acceleration" of cancer cell cycle times to their fastest, uniform rate. Angiogenesis inhibitors are administered starting 2-3 weeks prior to, and throughout, the regimen to insure G-Phase arrest and S-Phase depletion in tumor blood vessel cells during the regimen.

Tumor blood vessel (endothelial) cells are under VEGF stimulation, are an actively cycling population, and as such are subject to the cytotoxic effects of the S-Phase cytotoxic chemotherapy. Killing tumor vasculature would result in restricted blood flow. Restricted blood flow is one of the major density related stasis points. Stasis prevents phase specific, cell cycle active chemotherapy from functioning, both mechanistically and from a phase synchronicity perspective. Restricted blood flow also impairs deliver of chemotherapy. Accordingly, the importance of VEGF blockers to present invention is that they are used to protect tumor vasculature from chemotherapy. A well vascularized, depopulated tumor is a uniformly cycling tumor, which is easy to kill.

3) Prior Art Receptor Inhibitor Protocols—Antagonistic Action

Receptor blockers (inhibitors) target specific receptors that a over expressed on tumors. There are many types of tyrosine kinase receptors in the body. One family, called human epidermal receptor family, or the HER family is often found overexpressed on tumors. The members of the HER family are HER1 (also called the Epidermal Growth Factor Receptor or EGFR), HER2 (also called ErbB2 or HER2/neu), HER3 (also called ErbB3) and HER4 (also called ErbB4).

Commercially available receptor inhibitors include receptor monoclonal antibodies (MAbs) and small molecule receptor inhibitors. MAb receptor inhibitors commercially available are Trastuzumab (Genentech's Herceptin) which is a HER2 antibody and cetuximab (ImClone's Erbitux) and panitumumab (Amgen's Vectibix) which are HER1 antibodies. Small molecule receptor inhibitors commercially available are gefitinib (AstraZeneca's Iressa) and erlotinib (Genentech's tarceva), both of which inhibit function of HER1.

Prior art protocols administer the receptor inhibitor as either a stand alone treatment option or concurrent with phase specific, cell cycle active chemotherapy. It is the concurrent use of receptor inhibitors with phase specific cytotoxics that is the focus of present invention.

Prior art protocols administer receptor inhibitors continuously over the course of a phase specific, cytotoxic protocol. Trastuzumab (Genentech's Herceptin), a HER2 receptor blocker, is administered every week concurrent with a legacy protocol that uses cycles of S-Phase specific or M-Phase specific chemotherapy (per the full prescribing information).

TABLE 3

Genentech's Trastuzumab Breast Cancer Protocols

| Drug | Drug Class | Schedule |
|---|---|---|
| Trastuzumab | G1-Phase Cytostatic | q week |
| Anthracycline | S-Phase Cytotoxic | q 21 days × 6 |
| Cyclophosphamide | Non-Phase Specific | q 21 days × 6 |
| | or | |
| Trastuzumab | G1-Phase Cytostatic | q week |
| Paclitaxel | M-Phase Cytotoxic | q 21 days × 6 |

Cetuximab (ImClone's Erbitux), a HER1 receptor blocker, is administered concurrent with an S-Phase cytotoxic (per the full prescribing information):

TABLE 4

ImClone's Cetuximab Colon Cancer Protocols

| Drug | Drug Class | Schedule |
|---|---|---|
| Cetuximab | G1-Phase Cytostatic | q week |
| Irinotecan | S-Phase Cytotoxic | 350 mg/m2 q 21 days |
| | | or |
| | | 180 mg/m2 q 2 weeks |
| | | or |
| | | 25 mg/m2 q week × 4 |

Erlotinib (Genentech's Tarceva), a small molecule HER1 receptor blocker, is administered concurrent with an S-Phase cytotoxic (per the full prescribing information):

TABLE 5

Genentech's Erlotinib Pancreatic Cancer Protocols

| Drug | Drug Class | Schedule |
|---|---|---|
| Erlotinib | G1-Phase Cytostatic | q day |
| Gemcitabine | S-Phase Cytotoxic | q week × 7 of 8 = Cycle 1 |
| | | q week × 3 of 4 = Cycle 2 onward |

Gefitinib (AstraZeneca's Iressa), an small molecule HER1 receptor blocker, is administered concurrent with S-Phase and M-Phase cytotoxics (per the full prescribing information):

TABLE 6

AstraZeneca's Gefitinib NSCLC Lung Cancer Protocols

| Drug | Drug Class | Schedule |
|---|---|---|
| Gefitinib | G1-Phase Cytostatic | q day |
| Gemcitabine | S-Phase Cytotoxic | |
| Cis-Platinum | Non Phase Specific | |
| | or | |
| Gefitinib | G1-Phase Cytostatic | q day |
| Paclitaxel | M-Phase Cytotoxic | |
| Carboplatin | Non Phase Specific | |

Panitumumab (Amgen's Vectibix) HER1 blocker has only been used as a single agent treatment (per the prescribing information).

Figure 18:
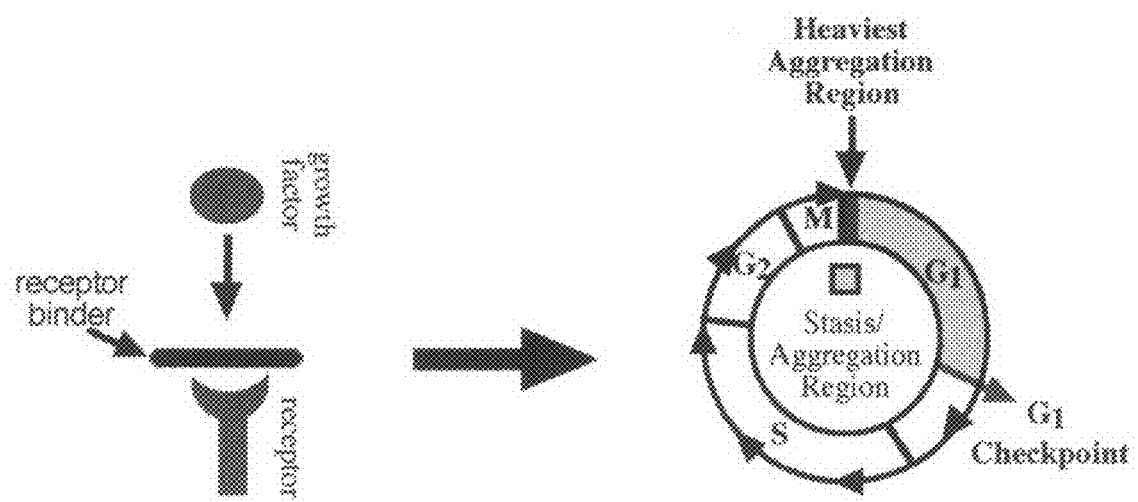
FIG. 18 shows the stasis region related to receptor inactivation.

Tyrosine kinase receptor inhibition (HER1, HER2, HER3, HER4) is cytostatic. G1-Phase cyclins are environment sensitive and have short terminal half lives. Cyclin D is environment sensitive, having a half life of only 15 minutes. Receptor inactivation translates into a drop in new Cyclin D production. Cyclin D levels (FIG. 2) drop quickly, preventing the cell from progressing further through the cell cycle. A cell that was pre the G1 checkpoint will arrest in the G-Phase. If the cell has already passed the G1 checkpoint, it will continue through the cell cycle and arrest as it enters the G1 Phase. Accordingly, cells will aggregate between the start of the G1 phase and the G1 checkpoint as shown in FIG. 18. This result in S-Phase and M-Phase depletion.

The G1 phase arrest is applicable to inhibition of any HER receptor type, as all use the same transduction pathways. The G1 phase arrest of FIG. 18 is also applicable to any transduction molecule inhibitors that target any of the pathways or molecules shown in FIG. 1 (e.g. tyrosine kinase inhibitors) or any G1 Phase cyclin/cdk inhibitors that target any of the G1 cyclins, CDK, or cyclin/CDK complexes shown in FIG. 2 (Cyclin D or E, CDK 2, 4, 6).

This mechanistic expectation of G1 phase arrest was confirmed ex vivo by Bunn et. al. (Bunn P A Jr., et. al. Clin. Cancer Res. October 2001; 7(10):3239-50) for trastuzumab (HER2 blocker) as summarized "Furthermore, Trastuzumab produced a G(1) cell cycle arrest and growth inhibition only in cell lines expressing Her-2/neu."

The problem with the prior art protocols disclosed above, is that the continuous administration of a G1-Phase cytostatic concurrent with an S-Phase cytotoxic or M-Phase cytotoxic is antagonistic to all but the first administration of phase specific cytotoxic. G-Phase arrest results in S-Phase depletion and M-Phase depletion. The first administration of the G1 phase cytostatic concurrent with an S-Phase or M-Phase cytotoxic does not interfere with the function of the S-Phase or M-Phase cytotoxic as shown in FIGS. 19a and 19d respectively, and cells in those respective phases are eliminated by the phase specific cytotoxic. However, continued administration of the cytostatic, results in aggregation of cells between the start of the G1-Phase and the G1 checkpoint. For a tumor specific G1-Phase cytostatic, this results in depletion of tumor cells in the S-Phase and M-Phase as shown if FIGS. 19b and 19e, respectively. Subsequent administrations of S-Phase or M-Phase cytotoxic do nothing to the tumor as there are no cells in the S-Phase or M-Phase as shown if FIGS. 19c and 19f, respectively. However, actively cycling bone marrow cells are not aggregated, and subsequent administrations kill bone marrow cells that are in the S-Phase. Accordingly, subsequent administrations of S-Phase or M-Phase cytotoxics, concurrent with a tumor specific cytostatic, only result in harm (systemic toxicity), with no therapeutic benefit (because of phase depletion in the tumor.)

To see if the mechanistic prediction is supported by clinical observations, we can use Skipper log cell kill math and trastuzumab Phase III median survival data to see if the actual clinical data is consistent with the mechanistic prediction (using the same basic methodology as in the colon cancer example previously presented).

To use the Skipper log cell kill model, one of the variables we need to know is average breast cancer cell cycle time.

We estimated average breast cancer population division times (and hence cell cycle times) at around a month (~30 days) in '146 based on both BSC timelines (from the first internal metastatic mass to lethal burden) and based on mechanistic predictions. Mechanistically, HER2 receptors are a tyrosine kinase receptor (just like colon cancer cells) and follow the same pathways outlined in FIGS. 1-3. Accordingly, they can be expected to have a "baseline" cycle time of around 20 days, much like the colon cancer cells. However, because of the second set of cell cycle controls on most breast cancer cells (i.e. estrogen or progesterone receptor control), which is tied to the monthly ovulation cycle, the cell cycle time could be expected to be closer to a month. Mechanistically, endocrine dependent breast cancer cells could be expected to progress through the cell cycle at a roughly 20 day cell cycle time until they come to the G1/S-Phase boundary where they would arrest pending endocrine release, which on average would result in 30 days to complete the cell cycle.

Our mechanistic computation is also in line with in vitro, breast cancer biopsy data. Heavy (deuterated) water assays were used to calculate proliferation rates of breast cancer cell cycle times by Lisa M. Misell et. al. (Lisa M. Misell, E. Shelly Hwang, Alfred Au, Laura Esserman, and Marc K Hellerstein, "*Development of a novel method for measuring in vivo breast epithelial cell proliferation in humans*", Breast Cancer Research and Treatment (2005) 89:257-264). Simplistically, patients drink 50 ml of 70% $^2H_2O$ water per day for a period of time (typically 2 weeks or more) prior to biopsy, the $^2H$ isotope is incorporated into DNA during the S-Phase, a biopsy is taken from the tumor, DNA is extracted from these cells and run through a mass spectrometer to determine the synthesis rate (i.e. synthesis rate=% of new labeled DNA/ time). The data is presented as a % of new cells per day, which can be converted mathematically into cell cycle times.

Although the primary focus of the Misell et. al. study was to determine differences in normal breast cell proliferation rates between pre-menopausal and post-menopausal women, biopsies of breast cancer tissue were taken from 4 of the patients (Misell et. al. study, FIG. 5, P. 261). The values for % of new cells per day are taken visually from the graph and converted into an average Population Division Time (PDT) (i.e. 100% new cells required for one population division ÷ observed % new cells/day=PDT in days) and shown in TABLE 7 below:

TABLE 7

Breast Cancer Cell Cycle Times - Misell et. al. Study

|  | % new cells/day | PDT or Avg. Cell Cycle Time |
|---|---|---|
| Patient 1: | 3.33 | 30 days |
| Patient 2: | 6.67 | 15 days |
| Patient 3: | 2.50 | 40 days |
| Patient 4: | 2.33 | 43 days |
| Average |  | 32 days |

The range in cell cycle times is consistent with the lack of deference to where the biopsy was taken from (i.e. the denser core with the slower cycle times or the faster cycling periphery) and lack of deference to endocrine dependence and plasma endocrine levels during the period of deuterated water administration. The average cell cycle time of 32 days is consistent with both the BSC and mechanistic predictions of '146.

Using a cell cycle time of a month and the Skipper log cell kill model we can project the median survival using the antagonistic scenarios above and compare them to the actual median survival data, to see if the mechanistic expectation is corroborated empirically.

The median metastatic breast cancer survival data by regimen (per the full prescribing info.) is as follows:

TABLE 8

Median Survival by Protocol - Metastatic Breast Cancer

| Drug | Class | Schedule | Median Survival |
|---|---|---|---|
| Paclitaxel | M-Phase Cytotoxic | q 21 days × 6 | 18.4 months |
| Paclitaxel + Trastuzumab | M-Phase Cytotoxic | q 21 days × 6 | 22.1 months |
|  | G1-Phase Cytostatic | q week |  |
| A—Anthracycline + C—Cyclophosphamide | S-Phase Cytotoxic | q 21 days × 6 | 21.4 months |
|  | Non-Phase Specific | q 21 days × 6 |  |
| A—Anthracycline + C—Cyclophosphamide + T—Trastuzumab | S-Phase Cytotoxic | q 21 days × 6 | 26.8 months |
|  | Non-Phase Specific | q 21 days × 6 |  |
|  | G1-Phase Cytostatic | q week |  |

Individually, a cytostatic, such as trastuzumab, administered over 4 months, would be expected to extend life expectancy by ~4 months, the amount of the cellular arrest time.

Individually, an S-Phase cytotoxic administered asynchronously as in the trials would wipe out 32% of the tumor each time it was administered, times 6 administrations equals ~2 population division cycles (i.e. 6×32) and since population division time is a month, the increase in life expectancy would be 2 months.

Individually, an M-Phase cytotoxic's contribution would be 6×0.05=0.3 months.

A best supportive care (BSC) baseline, assuming no chemotherapy is administered, can be best estimated from the M-Phase only group: BSC=survival of 18.4 months minus 0.3 month M-Phase contribution=18.1 months BSC w/o chemotherapy.

The individual contribution of cyclophosphamide can be estimated from the AC group. The administrations of anthracycline (S-Phase cytotoxic) and cyclophosphamide (non-phase specific cytotoxic) combine a known projected benefit and an unknown benefit, respectively. The 21.4 median survival time of the AC arm is 3.3 months longer than the BSC baseline of 18.1 months. The 33 months=3.3 population cycles killed back over 6 administrations, which works out to a tumor population kill rate of 55% per administration (i.e. 3.3÷6). Since the S-Phase cytotoxic's kill rate is 32%, the additional 23% (i.e. 55%-32%) kill rate in the 68% of cells not in the S-Phase cells represents a 34% (23%÷68%) "stand alone" tumor kill rate for the non specific chemotherapeutic. The "stand alone" kill rate of 34% represents the individual contribution the non phase specific would make on its own, if the S-Phase cytotoxic had not been administered, masking part of the non phase specific kill rate related to cells in the S-Phase. In combination, since there is an overlap in cell killing in the S-Phase, the cumulative AC kill rate is 55% (versus the 32%+34%=66% sum of the individual kill rates).

Trastuzumab+M-Phase Cytotoxic, Antagonistic Scenario—22.1 month projected survival versus 22.1 month actual survival: Under the antagonistic scenario outlined in FIGS. 5-7 above, paclitaxel+trastuzumab are projected to increase life expectancy by ~4 months. The benefit is basically only related to trastuzumab's 4 month individual extension of life expectancy from its cytostatic effect. The only benefit of Paclitaxel (M-Phase specific) would come from the first administration, where the 5% tumor reduction would translate into a insignificant 0.05 month (1.5 days) added to life expectancy. Trastuzumab would arrest the one third of cells in the G-Phase (pre G1-checkpoint) and arrest all remaining cells over the next 20 days as they entered the G-Phase. Accordingly, adding only the 4 month projected increase in life expectancy from trastuzumab's cytostatic effect to the 18.1 BSC baseline equals 22.1 months (i.e. 4+18.1=22.1). This is consistent with the observed median survival of 22.1 months from TABLE 8.

Trastuzumab+S-Phase Antagonistic+Non Phase Specific Synergistic Scenario—26.2 month projected survival versus 26.8 month actual survival: The S-Phase cytotoxic (anthracycline) arm also used a non-phase specific chemotherapeutic (cyclophosphamide). The first administration of AC would kill back the tumor by 55% leaving 45% survivors. Trastuzumab would put the tumor in cellular arrest for the next 4 months and the next 5 administrations of the S-Phase specific chemotherapeutic would provide 0 tumor kill rate as the tumor cells would all be arrested in the G Phase. Cyclophosphamide, on the other hand, is an alkylating agent, and alkylation of DNA can occur at any phase of the cell cycle. DNA damage would continue to accumulate with successive administrations, however actual cell death from the accumulated damage would likely not occur until the cells resumed cycling and encountered genotoxic checkpoints, at which time the doomed cells would be removed. Successive administrations are mathematically projected at inflicting 34% mortal damage (as computed previously) to "surviving cells", according to the Skipper log cell kill methodology, where surviving cells are meant to be cells that have not yet accumulated enough genetic damage to die when cycling is resumed and genotoxic checkpoints are encountered. This is shown in TABLE 9 below:

REDUCTION TO PRACTICE EXAMPLES

Examples 1-3 below are for illustrative purposes. The use prior art S-Phase cytotoxic regimens, modified for interlaced administration of HER1 blockers under present invention versus prior art's continuous, concurrent administration, and modified to eliminate endocrine stasis per '146 as well as provide enhanced "dual" aggregation/better tumor specificity by integrating '146 protocols. They are only intended to show why present invention's methods are better than prior art.

Examples 4-6 are the preferred embodiments of present invention. They combine all of the disclosures made in the specifications related to why chemotherapy fails to cure cancer. They are at the most comprehensive embodiments of present invention, are different from prior art in several respects, and are intended to provide the best possible protocol for achieving curative outcome. In the worst case, they should extend median survival by several years for a course of chemotherapy versus prior art's several month's extension of median survival. Although the examples are for HER1+ or HER2+ cancers or inappropriate growths, and use HER1 or HER 2 receptor blockers, the scope is intended to apply to any HER+ cancers or growths, by substituting the respective HER receptor blocker (inactivator), and using the same methodology as used in the representative examples for the HER1+ cancers or growths.

Example 7 is for HER2+ cancers or hyperproliferative growths. Numerous other protocols for cancers overexpressing HER2 receptor are covered by the parent application.

TABLE 9

| Projected Log Cell Kill Model for trastuzumab + AC | | | |
|---|---|---|---|
| Cycle | Functional Chemo(s) | Kill % | Survivors % |
| 1 | AC | 55% | 45.0% |
| 2 | C | 34% | 29.7% |
| 3 | C | 34% | 19.6% |
| 4 | C | 34% | 12.9% |
| 5 | C | 34% | 8.5% |
| 6 | C | 34% | 5.6% |

The 5.6% "survivable cells" at the end of the regimen would take 4.12 population cycles to get back to 100% (i.e. 5.6 to 11.2, 22.4, 44.8, 89.6, 179). The addition in life expectancy from the chemotherapeutic kill back would be 4.1 months (i.e. 4.1 population divisions×1 month cell cycle time). Thus, the total increase in average life expectancy would be 4 months from trastuzumab's cytostatic effect plus 4.1 months from the tumor kill back, for a total of 8.1 months over the BSC, or 26.2 month projected survival time (8.1+ 18.1 BSC=26.2) versus the 26.8 observed (TABLE 8).

Figure 20:
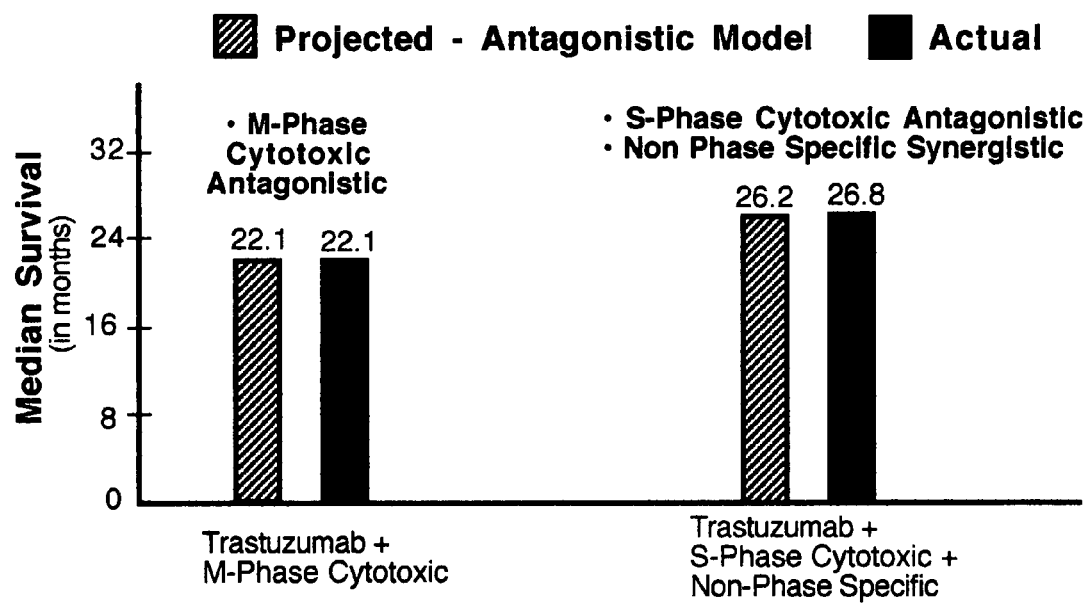
FIG. 20 graphically shows the antagonistic median survival prediction compared to the actual Phase III median survival data.

The comparison of predicted average life expectancy under the M-Phase cytotoxic antagonistic and S-Phase cytotoxic antagonistic, as compared to actual medial survival data, is presented in FIG. 20. The Phase III median survival data is consistent with antagonistic function of trastuzumab (a cytostatic) with subsequent administrations of S-Phase or M-Phase cell cycle active cytotoxics. The implication is that subsequent administrations of phase specific cytotoxics provide no therapeutic benefit but only result in unnecessary systemic toxicity.

Because the same G1-Phase stasis will be caused by any tumor specific growth factor receptor inhibitor, or growth factor antibody, or transduction molecule inhibitor (e.g. kinase inhibitor), or cyclin or CDK inhibitor, the use of prior art protocols for any of the aforementioned compounds will result in the same antagonistic action as shown in FIGS. 19a through 19f.

EXAMPLE 1

Erlotinib and Prior Art S-Phase Cytotoxic Schedule

A patient presents with inoperable, metastatic breast cancer that is estrogen and progesterone independent (i.e. ER– and PR–). A positive EGFR (HER1+) overexpression status is determined, as defined in the erlotinib prescribing information (i.e. at least 10% of cells staining for EGFR using the EGFR pharmDx kit).

Under prior art, the patient would be put on an asynchronous, endocrine insensitive regimen such as Anthracycline (S-Phase cytotoxic) plus Cyclophosphamide (Non phase specific) administered every 21 days, or worse, the patient could also be put on an asynchronous, endocrine insensitive, fairly meaningless 5% tumor kill back per administration regimen, using an M-Phase cytotoxic such as paclitaxel administered every 21 days. Alternatively, per the erlotinib (HER1 blocker) prescribing information, erlotinib (150 mg. oral dose) would be administered daily as either single agent treatment option (as used for lung cancer) or daily, concurrent with a weekly course of S-Phase cytotoxic chemotherapy such as gemcitabine (as used for pancreatic cancer in the prescribing information).

Under present invention, erlotinib (150 mg. oral dose) is used interlaced with an S-Phase cytotoxic chemotherapeutic. The following is a representative example of a interlaced (versus concurrent) erlotinib schedule. It does not matter which cancer it is used against, only that the cancer is HER1+, endocrine independent, and follows a typical "4 day fastest" cell cycle time as previously disclosed.

TABLE 10

Modified Prior art HER1+ Protocol

| Drug | Drug Class | Schedule |
|---|---|---|
| 21 day cycle | | |
| Irinotecan (30 mg/m2 IV qd) | S-Phase Cytotoxic | day 1-3 |
| Erlotinib (150 mg PO qd) | G1-Phase Cytostatic | day 3-16 |

Rationale: The schedule of present invention interlaces the administrations so that the G1-Phase cytostatic (erlotinib) is inactive one day or more prior to the administration of the subsequent S-Phase cytotoxic. Erlotinib has a half life of 1.5 days, and using ~3.5 half lives=functional terminal half life rule of thumb, puts the functional inactivation time roughly one day prior to the administration of the S-Phase cytotoxic. This allows the tumor cells that have been aggregated in the G-Phase to resume cycling and enter the S-Phase, where they can be killed by the subsequent administration of the S-Phase cytotoxic. The three administrations are used to cover the variability of inactivation time, variability of resumption of cycling, and span the time from when the leading edge of the cells (those arrested at the G1 checkpoint) and the trailing edge (those arrested at the start of the G-Phase) passing through the S-Phase. The cycle is repeated to progressively aggregate survivors, release them, and kill them.

This is in contrast to prior art protocols that administer the erlotinib daily over the entire course of the regimen, which results in G-1 phase aggregation and S-Phase depletion of tumor cells, with the consequence that all subsequent administrations of S-Phase cytotoxic result only in systemic toxicity (harm) without therapeutic benefit.

Advantages Over Prior Art: The simplest improvement of present invention over prior art is that subsequent administrations of S-Phase cytotoxic result in therapeutic benefit instead of just systemic toxicity.

A more profound improvement over prior art is that the G1-Phase cytostatic is now being used to limit tumor regrowth between administrations (a fundamental requirement of the Skipper log cell kill model), to progressively aggregate cancer cells in the G-1 phase, and to release the aggregated cells in a manner that progressively results in larger S-Phase fractions for enhanced tumor kill rates per each administration of S-Phase cytotoxic chemotherapy (i.e. FIGS. 16a and 16b as progressive elimination of stasis points and prevention of their reestablishment results in progressively more of the tumor cycling at the fastest rate inherent in its genetic mutation profile).

Alternate Embodiments

It should be noted that the above is only a representative example, based on average inactivation times of erlotinib, based on average "rules of thumb" for terminal half lives, and based on "average" and "fastest" cell cycle times for tyrosine kinase receptor mutations as disclosed in the specification section of this application. It is not meant to imply an absolute "optimal regimen" but only as an example that an "interlaced" regimen is better than the prior art "concurrent" regimens. Adjustments can be made if more precise or personalized data from a patient is available. As an example, the terminal half life of erlotinib was approximated in the above example, however much better approach would be to use a Positron Emission Tomography (PET) scan with a glucose tracer. Actively proliferating cancer cells use large amounts of glucose to fuel their growth and a PET scan with a glucose tracer would reveal if the arrested cancer cells had resumed cycling yet. Likewise, heavy water assay biopsies from pre 1 cc tumors or periphery of tumors larger than 1 cc would provide precise "fastest cancer cell cycle times" as previously described. Combining heavy water assay data and PET scan data would provide exceptionally accurate protocol schedules.

Also, innumerable combinations of different dose levels and frequency of administration of erlotinib may be used to achieve the same result of "aggregation and release" relative to subsequent administrations of S-Phase cytotoxic. The cytotoxic administrations are not limited to 21 administration cycles, but may be scheduled using any suitable administration interval, as long as they are synchronous with the "aggregation and release" schedule of the erlotinib. Depending on systemic toxicity issues, S-Phase cytotoxic administrations may be delayed a week or two to allow for recovery, with the HER1 blocker administration adjusted accordingly to keep the cancer cells aggregated until the next administration of S-Phase cytotoxic. The administration intervals of the both the erlotinib "aggregation and release" and S-Phase cytotoxic do not need to be fixed over the course or a regimen. "Gompertzian sensitive" regimens may start out with longer administration intervals at the start of the regimen, with the frequency of the administration intervals decreasing in proportion to the acceleration in overall tumor cell cycle times as stasis point are progressively removed and cell cycle times accelerate to the fastest rate inherent in their genetic mutation profile. The example also uses a single agent S-Phase cytotoxic, however a combination of S-Phase cytotoxic agents may be used. Any suitable dose of erlotinib or S-Phase cytotoxic may be used in the protocols.

The only guiding factor is that the erlotinib "aggregate and release" intervals are synergistically synchronous to subsequent administrations of S-Phase cytotoxic. This is in contrast to prior art protocols that only aggregate, but never release, tumor cells.

EXAMPLE 2

Erlotinib and Estrogen Dependent Breast Cancer

A patient presents with metastatic breast cancer that is estrogen dependent (i.e. ER+ and PR−). A positive EGFR overexpression (HER1+) status is determined, as defined in the erlotinib prescribing information (i.e. at least 10% of cells staining for EGFR using the EGFR pharmDx kit).

Under prior art, the patient would be put on an asynchronous, endocrine insensitive regimen such as Anthracycline (S-Phase cytotoxic) plus Cyclophosphamide (Non phase specific) administered every 21 days, or worse, the patient could also be put on an asynchronous, endocrine insensitive, fairly meaningless 5% tumor kill back per administration regimen, using an M-Phase cytotoxic such as paclitaxel administered every 21 days. Likewise based on prior art teachings of HER blockers, the patient would be put on a single agent HER blocker regimen or on a regimen that administers the HER blocker concurrent with a course of phase specific, cell cycle active chemotherapy.

Under present invention, the administrations of HER blockers are interlaced so as not to interfere with the function of subsequent administration of S-Phase cytotoxics, as presented in example 1. Furthermore, methods of U.S. Pat. No. 6,486,146 ('146), claims 1-4, are integrated into the instant protocols to insure functionality of the S-Phase cytotoxic in light of the cancer's endocrine dependence. Estrogen administration is used prior to administration of the S-Phase cytotoxic to sweep cells naturally aggregated at the G1/S-Phase boundary into the S-Phase, to insure their progression through the S-Phase, and to enhance function to the S-Phase cytotoxic's MOA, as covered by '146. No S-Phase cytotoxic can be expected to function reliably in an endocrine dependent cancer without a prior endocrine stasis "release".

In the reduction to practice example, the estrogen used is a 0.10 mg estradiol (E2) transdermal patch however any suitable substitute may be used that is capable of maintaining serum estradiol levels at 0.3 ng/ml or better, starting prior to the administration of the S-Phase cytotoxic and lasting through the terminal half life of the S-Phase cytotoxic. A study (Ginsburg et. al., "*Half life of Estradiol in Postmenopausal Women*", Gynecologic and Obstetric Investigation, 1998; 45.45-48) showed that administration of the E2 patch for thirteen hours resulted in an escalation of serum estrogen levels from a baseline of 19 pg/ml to 112 pg/ml. The mean half life of E2 after removal of the transdermal patch was 2.7 hours (which puts the terminal half life at around 9 hours). For estrogen dependent cancers, 3 such E2 patches, applied approximately 1 day prior to the first administration of the S-Phase cytotoxic in each cycle, and continued until the terminal half life of the last administration of the S-Phase cytotoxic in each cycle, can be used to insure elimination of any potential estrogen dependent stasis issues. Since each patch results in an approximately 100 pg/ml rise in estradiol blood levels, the three patches would boost the blood levels by 300 pg/ml (i.e. 0.3 ng/ml) which is the highest level (spike) of estradiol that occurs during the natural menstrual cycle as shown in FIG. 6b. This highest spike would ensure elimination of the endocrine dependent stasis point, sweeping cells arrested at the G1/S-Phase boundary into the S-Phase as well as insuring progression of cells through the S-Phase.

In the reduction to practice examples, the estrogen used is a 0.10 mg estradiol (E2) transdermal patch however any suitable substitute may be used that is capable of maintaining serum estradiol levels at 0.3 ng/ml or better, starting prior to the administration of the S-Phase cytotoxic and lasting through the terminal half life of the S-Phase cytotoxic. Numerous estrogen substitutes are available and include Estrace, Cenestin, Enjuvia, Femtrace, Gynodiol, Menest etc. . . . .

A representative protocol is presented below:

TABLE 11

Estrogen Dependent Cancer Protocol

| Drug | Drug Class | Schedule |
|---|---|---|
| 21 day cycle | | |
| Estradiol (3 × Patch) | Endocrine Hormone | day 1-2 |
| Irinotecan (50 mg/m2 IV qd) | S-Phase Cytotoxic | day 1-2 |
| Erlotinib (150 mg PO qd) | G1-Phase Cytostatic | day 3-16 |
| Estradiol (3 × Patch) | Endocrine Hormone | day 21 |

Advantages Over Prior Art: The representative example has all of the advantages over prior art as disclosed in Example 1 above, plus has the advantage of eliminating endocrine deficit related stasis issues (FIGS. 11a and 11b) that would prevent function of S-Phase cytotoxics.

Alternative Embodiments

The same innumerable alternative embodiments listed in Example 1 also apply to this Example 2, plus the potential for numerous endocrine drugs, doses, and schedules.

EXAMPLE 3

Erlotinib and Estrogen Dependent Breast Cancer

A post menopausal patient presents with metastatic breast cancer that is estrogen dependent (i.e. ER+ and PR−). A positive EGFR overexpression (HER1+) status is determined, as defined in the erlotinib prescribing information (i.e. at least 10% of cells staining for EGFR using the EGFR pharmDx kit).

Under prior art, the patient would be put on an asynchronous, endocrine insensitive regimen such as Anthracycline (S-Phase cytotoxic) plus Cyclophosphamide (Non phase specific) administered every 21 days, or worse, the patient could also be put on an asynchronous, endocrine insensitive, fairly meaningless 5% tumor kill back per administration regimen, using an M-Phase cytotoxic such as paclitaxel administered every 21 days. Likewise based on prior art teachings of HER blockers, the patient would be put on a single agent HER blocker regimen or on a regimen that administers the HER blocker concurrent with a course of phase specific, cell cycle active chemotherapy.

Under present invention, the administrations of HER blockers are interlaced so as not to interfere with the function of subsequent administration of S-Phase cytotoxics, as presented in example 1. Furthermore, methods of U.S. Pat. No. 6,486,146 ('146), claims 5-8, are integrated into the instant protocols. The administration of estrogen is used to insure function of the S-Phase cytotoxic in depopulating the tumor as discussed in Example 2. The administration of estrogen downregulators is used in Example 3 to further enhance G1-Phase arrest (in addition to the erlotinib's G1-Phase arrest) in order to limit tumor regrowth, prevent reestablishment of unwanted stasis points, and facilitate subsequent synchronicity to the S-Phase cytotoxic. As a representative example of post menopausal estrogen downregulator, a 25 mg oral exemestane dose (Pfizer's Aromasin) is used, however any other suitable aromatase inhibitor could be used (e.g. 1 mg anastrozole tablet, 2.5 mg letrozole tablet).

A representative protocol is presented below:

TABLE 12

Estrogen Dependent Cancer Protocol

| Drug | Drug Class | Schedule |
| --- | --- | --- |
| 21 day cycle | | |
| Exemestane (25 mg PO qd) | Aromatase Inhibitor | day 1-21 |
| Estradiol (3 × Patch) | Endocrine Hormone | day 1-2 |
| Irinotecan (50 mg/m2 IV qd) | S-Phase Cytotoxic | day 1-2 |
| Erlotinib (150 mg PO qd) | G1-Phase Cytostatic | day 3-14 |
| Estradiol (3 × Patch) | Endocrine Hormone | day 21 |

Rationale: The rationale of adding the aromatase inhibitor is to provide a "dual action", tumor specific, G1 phase arrest from the erlotinib/exemestane combination as well as to provide a much more precise estrogen "release" into the S-Phase (versus using erlotinib's approximate inactivation time release method). Furthermore, the above schedule also minimizes toxicity to non malignant, HER1 expressing cells, that have also been aggregated. The erlotinib is discontinued a few days earlier (in the above table) to avoid any potential interference with the more precise estrogen release and to insure non malignant, non estrogen dependent, HER1 expressing cells resume cycling and pass the S-Phase (or at least become asynchronous) prior to the administration of the S-Phase cytotoxic. In contrast, the cancer cells are only allowed to progress to the next stasis point at the G1/S-Phase boundary, awaiting subsequent estradiol release in conjunction with the administration of the S-Phase cytotoxic.

If the patient is pre menopausal and has functioning ovaries, ovarian estrogen downregulators would be used over the course of the regimen. An example of such an estrogen down-regulator is AstraZeneca's Zoladex (3.6 mg goserelin acetate implant) that suppresses pituitary gonadotropins and decreases serum estradiol levels consistent with the postmenopausal state. Zoladex's initial, transient increase in serum estradiol levels at the start of the regimen can be matched to the first administration of S-Phase cytotoxic and its subsequent estradiol downregulation allows the patient to be treated as if they were post menopausal, as in Table 12 above.

EXAMPLE 4

Preferred Embodiment

HER1+ Protocols—Non Endocrine Hormone Dependent Growths

A patient presents with cancer or a hyperproliferative growth that over expresses EGFR (HER1+). Representative examples include, but are not limited to, colon cancer, lung cancer, head and neck cancer, pancreatic cancer, bladder cancer brain cancer, breast cancer, and non malignant hyperproliferative growths such as endometriosis and enlarged prostate (BPH).

Under prior art, the cancer patients would be put on an asynchronous chemotherapeutic regimen such as Irinotecan's (S-Phase cytotoxic) administered for one or more cycles of weekly administration for 3 of 4 weeks. In clinical trials, the HER1 receptor blocker Cetuximab (Imclone's Erbitux) was administered concurrent with the S-Phase cytotoxic irinotecan as is practice under prior art (per the cetuximab prescribing information) and the conclusion was that "Currently, no data are available that demonstrate an improvement in disease-related symptoms or increased survival with ERBITUX for the treatment of EGFR-expressing, metastatic colorectal carcinoma".

Under present invention, a HER1 receptor blocker is used interlaced with the S-Phase cytotoxic to provide synergistic effect versus prior art's antagonistic effect. Rifampicin is administered prior to the administration of the S-Phase cytotoxic to provide a more precise "release" of aggregated cells. Rifampicin increased clearance of erlotinib by 3 fold and reduced AUC by ⅔ (per erlotinib prescribing information). Rifampicin is available from Ciba as Rimactazid 150 and Rimactazid 300 capsules or from Merrell as Rifinah 150 and Rifinah 300. Rifampicin is used in the treatment of tuberculosis, where it inhibits bacterial RNA-polymerase. As an inactivator of erlotinib, it functions as a inducer of CYP3A4, the predominant enzyme involved in erlotinib metabolism. HER1 ligands may also be administered to insure a more precise "release" of aggregated cells. Known HER1 ligands include epidermal growth factor (EGR), transforming growth factor alpha, amphiregulin, betacellulin, heparin-binding EGF-like growth factor (HB-EGF), and epiregulin.

As a representative example:

TABLE 13

HER1+ Cancer Protocol

| Drug | Drug Class | Schedule |
| --- | --- | --- |
| Monthly (30 day) Cycle | | |
| Irinotecan (50 mg/m2 IV qd) | S-Phase Cytotoxic | day 1-2 |
| Erlotinib (150 mg PO qd) | G1-Phase Cytostatic | day 2-27 |
| Rimactazid (600 mg PO) | Erlotinib inactivator | day 30 |

Rationale: In the first cycle, the administrations of S-Phase cytotoxic (days 1-2) depopulates most of the fastest cyclers and part of the slower cyclers. In subsequent cycles the 2 administrations of S-Phase cytotoxic are used to compensate for variability in erlotinib inactivation time and progression time of the leading and trailing edge of the cells aggregated across the G1 phase. The administration of the erlotinib on day 2 is given prior to, or concurrent with, the S-Phase cytotoxic and is used to arrest cancer cells at the G1-checkpoint. The continued use of erlotinib for the next several weeks functions to aggregate surviving cancer cells between the start of the G-Phase and the G1-checkpoint. The last administration of erlotinib on day 27 is 5 days (approximate terminal half life) prior to the start of the next cycle of S-Phase cytotoxic (i.e. day 1 of next cycle=day 31 of prior cycle). The administration of rifampicin on day 30 provides much more decisive inactivation of erlotinib and hence a more precise "release" of the cancer cells relative to the administration of S-Phase cytotoxic.

The above is only one representative example of innumerable possibilities, as erlotinib administrations may be discontinued earlier or later than day 27, rifampicin may be administered in multiple administrations and doses, over multiple days, starting one or more days prior to the administration of the S-Phase cytotoxic and lasting up to or through the entire S-Phase cytotoxic administration schedule. Innumerable variants of S-Phase cytotoxics and doses, and combinations of S-Phase cytotoxics, are also possible (e.g. Etoposide 100-150 mg/m2 IV qd×1-5 d, Idarubicin 10 mg/m2 IV qd×1-3, Amsacrine 100-150 mg/m2 IV qd×1-5 etc. . . . ). Low potency (i.e. low in phase kill rate) cytotoxics such as 5FU (fluorouracil) are not recommended, particularly as a single agent treatment. Dietary restrictions would likely be required over the course of the S-Phase cytotoxic and up to a day or two after, because of gastrointestinal cytotoxicity. Innumerable variants of the protocols of TABLE 13 are also possible. As an example, the preferred embodiment of the protocol is shown in TABLE 14, which also administers the Rimactazid into the start of subsequent S-Phase cytotoxic administrations (i.e. versus TABLE 13) plus administers one or more of the 6 known HER1 ligands, plus resumes erlotinib administration a few days after the S-Phase cytotoxic to allow for recovery of non malignant HER1 cell populations:

TABLE 14

Preferred Embodiment of HER1+ Cancer Protocol

| Drug | Drug Class | Schedule |
|---|---|---|
| First monthly (30 day) Cycle: | | |
| Irinotecan (50 mg/m2 IV qd) | S-Phase Cytotoxic | day 1-2 |
| Erlotinib (150 mg PO qd) | G1-Phase Cytostatic | day 2-26 |
| Rimactazid (600 mg PO) + ligand | Erlotinib inactivator | day 30 |
| Next Monthly (30 day) Cycles (i.e. cycles 2 thru N): | | |
| Rimactazid (300 mg PO) + ligand | Erlotinib inactivator | day 1-2 |
| Irinotecan (50 mg/m2 IV qd) | S-Phase Cytotoxic | day 1-2 |
| Erlotinib (150 mg PO qd) | G1-Phase Cytostatic | day 4-26 |
| Rimactazid (600 mg PO) + ligand | Erlotinib inactivator | day 30 |

In the preferred embodiment, the administration of rimactazid, or rimactazid plus ligand, relative to the administration of the S-Phase cytotoxic, is done so that therapeutically effective serum levels are achieved not more than 0.4 multiplied by the fastest cancer cell cycle time inherent in the cancer's genetic mutation profile (i.e. approximately the G1 checkpoint through "end of S-Phase" transit time) so that no aggregated cancer cells escape the S-Phase prior to the first administration of the S-Phase cytotoxic. The fastest cell cycle times can be obtained by heavy water assays from a pre 1 cc tumor, or periphery of a post 1 cc tumor, as previously described in the specification section. Alternatively, approximate "fastest cell cycle" time data may be used (e.g. as disclosed in the specifications) and the number of S-Phase cytotoxic administrations can be increased to compensate for the lower accuracy (e.g. daily S-Phase cytotoxic administrations for 3 to 5 days) and the rest of the schedule adjusted accordingly. Resumption of cancer cell cycling can also be ascertained by PET (Positron Emission Tomography) with a glucose tracer (as discussed in Example 1), to further improve accuracy of the relative administrations in the protocol. More precise information also allows for release of aggregated normal one day, HER1 expressing cyclers, so they escape the first administration of S-Phase cytotoxic (or become asynchronous), without the slower cycling cancer cells escaping the first administration of S-Phase cytotoxic.

The administrations of erlotinib are resumed a few days after the S-Phase cytotoxic to allow for recovery of normal HER1 expressing active cycling cell populations such as skin or G1 tact (i.e. one day cyclers) but still arrests the "fastest" 4 day cycling "S-Phase survivor" cancer cells prior to them reaching the G1 checkpoint (or at least limits the fastest cycling surviving cancer cells to not more than one cell cycle). However, any suitable schedule may be substituted.

The cycles do not need to be "monthly cycles", they could just as easily be "semimonthly", or any other suitable time frame, as long as the "cancer aggregation and release" is timed appropriately relative to the administration(s) of S-Phase cytotoxic.

Other HER1 receptor blockers and methods of reversing receptor blockers could be substituted in the above example. Several other commercially available HER1 receptor blockers were previously listed in the specifications and include cetuximab, gefitinib, panitumumab and several other HER1 inhibitors/inactivators are currently in clinical trials. Known HER1 ligands include epidermal growth factor, transforming growth factor alpha, amphiregulin, betacellulin, heparin-binding EGF-like growth factor, and epiregulin. A stand alone use of HER1 ligands (i.e. without rifampicin) would administer them starting preferably toward the end of terminal half life of the receptor binder (prior to the administration of the S-Phase cytotoxic) and lasting into the S-Phase cytotoxic schedule.

The above cycles (either TABLE 13 or TABLE 14 or any variant thereof) are repeated several times with the intent of progressive reduction of tumor size, elimination of density related stasis points, and acceleration of all cell cycle times to the fastest possible rate inherent in their genetic mutation profile as shown in FIGS. 16a and 16b. As previously disclosed, a uniformly cycling tumor is easy to kill using various protocols, including simple S-Phase cytotoxic administration intervals that are synchronous to the fastest possible cancer cell cycle time (e.g. 4 day cell cycle time) and asynchronous to normal actively cycling cells (e.g. 1 day cell cycle time). The latter regimen has been previously described in the specifications and a regimen that is synchronous to the uniformly cycling cancer cells results in the textbook "staircase" pattern of FIG. 8b for the cancer and its asynchronicity to normal actively cycling cells results in a "saw tooth" pattern of FIG. 14 for the normal active cyclers—a condition from which they readily recover (in basically the same way cancer cells readily recover from today's asynchronous chemotherapy regimens).

Advantages Over Prior Art: First, the simplest improvement of present invention's interlaced administrations, over prior art's concurrent administrations, is that subsequent administrations of S-Phase cytotoxic result in therapeutic benefit in present invention instead of just systemic toxicity as under prior art.

Second, a more profound improvement over prior art is that the G1-Phase cytostatic is now being used to limit tumor regrowth between administrations (a fundamental requirement of the Skipper log cell kill model), to progressively remove density related stasis points, to progressively aggregate more cancer cells in the G-1 phase, and to release the aggregated cells in a manner that results in progressively larger S-Phase fractions for enhanced tumor kill rates per each administration of S-Phase cytotoxic chemotherapy (i.e. FIGS. 16a and 16b).

However, the third and most important improvement, is that protocols of present invention work to progressively eliminate heterogeneity of cell cycle times inherent in a tumor and as a consequence eliminate the inherent asynchronicity of the progression of the S-Phase in cancer cells relative to subsequent administrations of S-Phase cytotoxic. Prior art has not yet recognized that 1) heterogeneity of cell cycle times in a tumor and 2) Gompertzian related acceleration in cell cycle times from tumor size reduction, are the reasons why all of today's phase specific chemotherapeutic protocols are asynchronous to the cancer cell population and that this is why the prior art protocols fail to achieve appreciable curative outcome. The protocols outlined above solve this problem for cancers that over express on or more growth factor receptor types.

Although the example above if for HER1 overexpression, a similar regimen may just as easily be constructed for any receptor overexpressing tumor. As an example, for a HER2 overexpressing tumor, trastuzumab (Genentech's Herceptin) could be used in a similar manner to provide the same 3 benefits over prior art protocols. The discontinuation time of trastuzumab prior to S-Phase cytotoxic administration would be adjusted for trastuzumab's terminal half life. The above protocol is not limited to cancer type, but to genetic mutation profile (i.e. HER1, HER2, HER3, or HER4 overexpression profile). The more important element is knowing the "fastest cell cycle time" if a stand alone S-Phase cytotoxic regimen is substituted after several cycles of interlaced protocols as outlined in TABLE 13 or 14. As disclosed in specifications, deuterated water assays are an accurate method of ascertaining cell cycle times. A "fastest cell cycle time" could obtained from biopsies taken form a pre 1 cc size tumor or from the extreme periphery of a post 1 cc size tumor. Highly personalized, highly accurate, information like this would greatly increase the probability of curative outcome if a synchronous S-Phase cytotoxic protocol is substituted at the end of the regimen as described above.

Cancers that over express more than one growth factor receptor (e.g. HER1+ and HER2+) can be treated with both HER1 and HER2 blockers using the protocols of present invention. Preferred embodiment would minimize systemic toxicity by discontinuation the HER1 blocker first (to allow asynchronicity of the active cyclers HER1 aggregates) followed by HER2 inactivation (because HER2 is much more tumor specific and does not aggregate active cyclers).

Last, the preferred embodiment of Example 4 also uses a VEGF inhibitor in order to protect tumor vascularization (not shown in the schedules above for simplicity, but discussed separately in Example 6).

EXAMPLE 5

Preferred Embodiment

HER1+Protocols for Endocrine Hormone Dependent Growths

A postmenopausal patient (or any patient where estrogen is not appreciably produced by the ovaries) presents with breast cancer, or other malignant or non malignant growth, that over expresses EGFR (HER1+) and that is also estrogen dependent (ER+) and progesterone receptor negative (PR−)

Under present invention, the protocols of Example 4 would be integrated with the protocols of '146 in the representative example below:

TABLE 15

Preferred HER1+, ER+ Cancer Protocol (postmenopausal)

| Drug | Drug Class | Schedule |
|---|---|---|
| First monthly (30 day) Cycle: | | |
| Estradiol (3 × Patch) | Endocrine Hormone | day 0-2 |
| Irinotecan (50 mg/m2 IV qd) | S-Phase Cytotoxic | day 1-2 |
| Erlotinib (150 mg PO qd) | G1-Phase Cytostatic | day 2-24 |
| Exemestane (25 mg PO qd) | Aromatase Inhibitor | day 1-30 |
| Rimactazid (600 mg PO qd) | Erlotinib inactivator | day 28-30 |
| Estradiol (3 × Patch) | Endocrine Hormone | day 30 |
| Next Monthly (30 day) Cycles (i.e. cycles 2 thru N): | | |
| Exemestane (25 mg PO qd) | Aromatase Inhibitor | day 1-30 |
| Estradiol (3 × Patch) | Endocrine Hormone | day 1-2 |
| Irinotecan (50 mg/m2 IV qd) | S-Phase Cytotoxic | day 1-2 |
| Erlotinib (150 mg PO qd) | G1-Phase Cytostatic | day 5-24 |
| Rimactazid (600 mg PO qd) | Erlotinib inactivator | day 28-30 |
| Estradiol (3 × Patch) | Endocrine Hormone | day 30 |

Rationale: The administration of estradiol prior to administration of the S-Phase cytotoxic sweeps any cancer cells aggregated at the G1/S-Phase boundary into the S-Phase and the administrations of estradiol into the S-Phase cytotoxic schedule insures progression of the cells through the S-Phase where they are killed.

The use of both aggregating agents, erlotinib and estrogen downregulation, provides a dual action G1—Phase and G1/S-Phase boundary aggregation, respectively. The erlotinib aggregation is released first (by Rimactazid) because the erlotinib related aggregation is at an earlier part of the G1-Phase (HER1 ligands may also be used to facilitate the HER1 blocker release as described in Example 4). This release allows the cells to progress to toward the second aggregation point (i.e. the G1/S-Phase boundary) where the cells are then more precisely released (by the estradiol) into the S-Phase, relative to the subsequent administrations of S-Phase cytotoxic. This also provides a time window in which any aggregated, non malignant, HER1 expressing, actively cycling cells (e.g. skin, hair, G1, etc. . . . that are one day cyclers) are released to pass through the S-Phase (or at least become asynchronous) before the S-Phase cytotoxic is administered, while the endocrine dependent cancer cells are arrested at the G1/S-Phase boundary for release into the S-Phase at a later point in time and do not escape the S-Phase cytotoxic. Likewise, the administration of erlotinib is not started until a few days after the S-Phase cytotoxic administrations in order to allow normal HER1 expressing active cyclers to recover, with the exemestane aggregating survivors at the G1/S-Phase boundary until the erlotinib administrations are once again resumed to provide the dual action aggregation.

In the preferred embodiment, the administration of the estradiol, relative to the first administration of the S-Phase cytotoxic, is done so that therapeutically effective serum estradiol levels are achieved not more than 0.32 multiplied by the fastest cancer cell cycle time inherent in the cancer's genetic mutation profile (i.e. effectively the S-Phase transit time) so that no aggregated cells escape the S-Phase prior to the first administration of the S-Phase cytotoxic, however any suitable timing may be used. PET scans with a glucose tracer are preferred method for determination of when the cancer cells have resumed cycling. The fastest cell cycle times can be obtained by deuterated water assays from a pre 1 cc tumor, or periphery of a post 1 cc tumor, as previously described in the specification section. Alternatively, average "fastest cell cycle" time data may be used (e.g. as disclosed in the specifications) and the number of S-Phase cytotoxic administrations can be increased to compensate for the lower accuracy (e.g. daily S-Phase cytotoxic administrations for 3 to 5 days of Irinotecan 30-50 mg/m2 IV qd, or other suitable S-Phase cytotoxic, with the first administration starting potentially as soon as a few hours after the first administration of the estradiol) and the rest of the schedule adjusted accordingly.

If the patient is pre menopausal and has functioning ovaries, any method of downregulation of estrogen production or blocking estrogen's function would be substituted for, or used concurrent with, the aromatase inhibitor. In the preferred embodiment, an estrogen downregulator such as AstraZeneca's Zoladex (3.6 mg goserelin acetate implant) that suppresses pituitary gonadotropins and decreases serum estradiol levels consistent with the postmenopausal state would be used throughout the regimen, concurrent with the aromatase inhibitor. The preferred approach is to eliminate all indigenous estrogen sources, leave estrogen receptors intact, and use exogenous administration of estradiol to "release" the aggregated cells at the opportunistic time relative to administration(s) of the S-Phase cytotoxic. The addition of Zoladex would effectively turn a pre menopausal woman into a postmenopausal woman, allowing treatment under TABLE 15 above. This is the cleanest, most precise method, of achieving the desired outcome. However, alternate approaches could also be employed, such as use of estrogen blockers (i.e. defined as anything that blocks the biological function of estrogen). Examples of estrogen blockers include estrogen receptor binders such as nolvadex (tamoxifen citrate) or toremifene (GTx, Inc.'s Fareston 88.5 mg. toremifene citrate) tablets which would be substituted for, or preferably used in conjunction with, the aromatase inhibitor (exemestane) with the days of administration of the estrogen blocker adjusted to match its terminal half life/inactivation time (i.e. so as not to interfere with the subsequent estradiol induced release) and potentially much larger doses of estradiol would being used to insure the "release" at the desired point in time. Toremifene is also metabolized by CYP3A4 (as is erlotinib) and accordingly the rifampicin (CYP3A4 upregulator) can be used as a "dual inactivator". SERMs (Selective Estrogen Receptor Modulators) that downregulate estrogen receptor production, such as fulvestrant (Astraeneca's Faslodex), should not be used unless estrogen receptor status can be restored prior to the administration of estradiol.

The "aggregation and release" cycles of the above protocol are intended to be repeated as in the prior examples to achieve a "uniformly cycling tumor".

The preferred embodiment of Example 5 also uses a VEGF blocker (not shown in the schedules above, but discussed separately in Example 6) in order to protect tumor vascularization.

EXAMPLE 6

Preferred Embodiment

All Protocols Integrate VEGF Inhibitor

Under preferred embodiment of present invention, a VEGF inhibitor such as bevacizumab (Genentech's Avastin), or any other suitable VEGF antibody or VEGF receptor inhibitor is used throughout the regimen, including the protocols disclosed in Example 4 and Example 5. However, in a break from prior art, the administration of bevacizumab under present invention is started prior to the start of the regimen (e.g. one or more weeks) and then continued throughout the course of the regimen, the latter part being consistent with prior art. The term VEGF blocker, as used in this application, is intended to encompass any drug that blocks the biological function of VEGF, as evidenced by endothelial (blood vessel cell) arrest (stasis).

Rationale: Under present invention, the VEGF blocker is used to protect the tumor vasculature from the cytotoxic effects of the S-Phase cytotoxic. Blood vessel (endothelial) cells are under VEGF stimulation from the tumor and as such are also an actively cycling cell population. Administration prior to the start of the regimen arrests blood vessel cells between the start of the G-Phase and the G1-checkpoint (VEGF is also receptor tyrosine kinase as shown in FIGS. 1-3) and allows cells at or past the G-1 checkpoint to progress through the S-Phase prior to the first administration of S-Phase cytotoxic. Continued administration prevents blood vessels from entering the S-Phase and hence protects them from being killed by the S-Phase cytotoxic (in a manner similar to how today's concurrent HER1 and HER2 blocker administrations protect cancer cells from being killed by S-Phase cytotoxics).

Protecting tumor vasculature is consistent with the goal of eliminating all stasis points and preventing their reestablishment in order to achieve the fastest, but homogenous, cell cycle time (as previously disclosed). Chemotherapeutic kill back of tumor vasculature would impair blood supply, and impaired blood supply is one of the major stasis points as previously disclosed and shown in FIG. 10a (i.e. impairs nutrient and oxygen delivery). Impaired vasculature also impairs delivery of endocrines in endocrine dependent cancers, and impairs delivery of all therapeutics including the chemotherapeutic. A well vascularized, well depopulated tumor, provides an environment where the uniform "fastest possible" cell cycle times are possible in all cancer cells. As previously disclosed, a tumor with uniform cell cycle times is easy to kill as synchronous administration intervals of S-Phase cytotoxics are possible (i.e. FIG. 8b) versus today's asynchronous administrations (i.e. FIG. 14).

EXAMPLE 7

HER2+ Protocols

A patient presents with a metastatic cancer that is HER2+ (HER2 overexpression).

Under prior art, the patient would be put on either a single agent HER2 receptor blocker regimen or on a combination regimen that administers the HER2 receptor blocker concurrent with a phase specific cytotoxic (i.e. as per trastuzumab prescribing information).

Under present invention, interlaced administrations of a HER2 receptor blocker such as Trastuzumab (Genentech's Herceptin) are used with an S-Phase cytotoxic chemotherapeutic.

As a representative example:

TABLE 15

HER2+ Cancer Protocol

| Drug | Drug Class | Schedule |
|---|---|---|
| Cycle 1: Monthly (30 day) Cycle: | | |
| Irinotecan's (30 mg/m2) | S-Phase Cytotoxic | day 1-3 |
| Trastuzumab (27 d t ½ dose) | G1-Phase Cytostatic | day 3 |
| No Drug | G1 release (in ~27 days) | day 30 |
| Cycle 2, day 1 starts on day 31 of Cycle 1 | | |
| Monthly Cycle 2-N: | | |
| Irinotecan (30 mg/m2) | S-Phase Cytotoxic | day 1-5 |
| Trastuzumab (26 d t ½ dose) | G1-Phase Cytostatic | day 4 |
| No Drug | G1 release (in ~26 days) | day 30 |

The dose of trastuzumab used is based on achieving a desired "stasis period" followed by "stasis release" that is timed to occur opportunistically relative to the next administration of S-Phase cytotoxic. A dose that approximates the desired terminal half life may be approximated from the data in the full prescribing information, as doses from 10 mg to 500 mg were characterized for pharmacokinetic purposes (half life averaged 1.7 days to 12 days at the 10 and 500 mg doses, respectively).

However, in the preferred embodiment a more accurate, personalized dose based on individual patient inactivation times would be used. It could be based on the same methods by which the pharmacokinetic data was obtained in the prescribing information (e.g. periodic measurement of serum concentrations of trastuzumab plus intracellular inactivation time) or any other suitable means of determining inactivation time and/or resumption of cell cycling. As another example, PET scans using a glucose tracer could be used to more precisely determine when the cancer cell population resumed cycling (and hence a more precise time for when the S-Phase cytotoxic should be administered). Patient personalized inactivation times would result in greatly improved performance of protocols of present invention and require many fewer cycles to achieve the objective of a depopulated, uniformly cycling tumor.

Many other examples of HER2+ cancer protocols are contained in the parent application.

SCOPE OF INVENTION

Alternate Examples

The above representative examples have innumerable variants and are not intended to limit the scope of the invention. Many of the potential alternate embodiments were mentioned in the Examples 1-7. Many more are also possible. The scope of the invention is intended to encompass the following:

1) The first and simplest embodiment over prior art is a protocol that uses interlaced administrations of receptor blockers versus the prior art practice of concurrent administration. The difference is synergistic, versus antagonistic function.

2) The second embodiment over prior art is using receptor blockers to limit tumor regrowth between administrations of cytotoxic chemotherapy (a fundamental requirement of the Skipper log cell kill model), to progressively remove density related stasis points and prevent their reestablishment, to progressively aggregate more cancer cells in the G-1 phase, and to release the aggregated cells in a manner that results in progressively larger S-Phase fractions for enhanced tumor kill rates per each administration of S-Phase cytotoxic chemotherapy (i.e. FIGS. 16a and 16b). This is in contrast to prior art's "S-Phase depletion" and no tumor kill back from subsequent administrations of S-Phase cytotoxic.

3) The third embodiment over prior art is the use of receptor inhibitors to progressively transform a tumor to where all of the cancer cells are cycling at a uniform, fastest possible rate. A uniformly cycling tumor is easy to eradicate completely, either through continued use of receptor inactivation synchronized protocols or by switching over to stand alone S-Phase cytotoxic protocols that are synchronous to the progression of the S-Phase in the cancer cell population but not synchronous to the progression of the S-Phase in normal actively cycling cells such as bone marrow.

SUMMARY OF NOVELTY AND UNOBVIOUSNESS

The first embodiment mentioned above (i.e. interlaced versus concurrent administrations) is unobvious because prior art does not even know it has a problem. If prior art practitioners were aware of the problem, they would be guilty of medical malpractice. As disclosed in instant application, concurrent administrations prevent subsequent administrations of phase specific cytotoxics from functioning, which result in no therapeutic benefit but only systemic toxicity (harm). Doing harm, with no commensurate therapeutic benefit, qualifies as medical malpractice. As such, a prima facie case for unobviousness of the first embodiment can be made.

The second embodiment is unobvious for the same reasons as the first embodiment as well as being additionally unobvious in context of prior art's failed attempts at "phase enrichment", which have poisoned the well for these types of protocols. Applicant has gone over numerous prior art attempts in the specifications, figured out why they failed, and disclosed "principles of tumor specific, cell cycle synchronous chemotherapy" that must be adhered to for successful protocols. The protocols presented in instant application adhere to these principles, in contrast to prior art protocols. In contrast to prior art's use of numerous non tumor specific aggregating agents, present invention uses tumor specific aggregating agents such as HER2 blockers and estrogen blockers, which require a cell 1) to posses the receptor, and 2) to be an actively cycling population—which makes the protocols fairly specific to the cancer cells described. HER1 is somewhat less specific, it is not expressed on bone marrow cells, however it is expressed on active cyclers such as skin and other epithelial cells (adverse skin and G1 events are common—e.g. Table 1, page 10, of Amgen's panitumumab prescribing information). However, the protocols of present invention make the HER1 blockers tumor specific by either arbitraging the disparity between the faster cell cycle times of normal active HER1 cyclers and the slower HER1+ cancer cells in the HER1 blocker "release" part of the regimen or alternatively in endocrine dependent cancers by using a second "aggregation and release" point that is tumor specific. The protocols of present invention are "Gompertzian/stasis sensitive" whereas prior art protocols were not. The instant invention "aggregates"

cells over a period of time related to the Gompertzian growth curve implied cell cycle time (versus prior arts Gompertzian oblivious "enrichment" concepts). Instant invention also provides a receptor specific "release" mechanism for more precise, tumor specific, synchronization relative to administrations of an S-Phase cytotoxic. The protocols of present invention are also endocrine sensitive, administering the requisite endocrine hormones to insure function of the S-Phase cytotoxics (today's regimens still do not give deference to this stasis issue). The regimens of present invention are Skipper compliant, as no breaks or drug vacations are allowed, in contrast to prior art protocols where the tumor can regrow, reestablish stasis points, and become asynchronous to the regimen. These numerous differences from prior art protocols make prima facie case for unobviousness for the second embodiment.

The third embodiment relates to regimens that progressively transform a tumor to where all the cancer cells are cycling at a uniform (albeit fastest possible) cell cycle time. The uniformly cycling cancer cell population is easy to eradicate completely. This is unobvious to prior art, as prior art is unaware of why prior art protocols fail to cure cancer. Applicant has put together several areas of science to disclose the mechanisms of stasis underlying Gompertzian growth, why they result in 1) heterogeneity of cell cycle times and 2) acceleration in cell cycle times from chemotherapeutic tumor depopulation, and why this results in asynchronicity of successive administrations of phase specific cytotoxic relative to the progression of the susceptible phase in the cancer cell population in prior art protocols. Applicant has then applied simple Skipper log cell kill math to existing Phase III data to corroborate the mechanistic predictions of asynchronicity. The absence of any successful, synchronous, Gompertzian/stasis sensitive, Skipper compliant, protocols as described above are the best proof of prior art's absence of understanding as to why their protocols only result in modest increases in median survival, yet those protocols are still used to this day. Present invention's concept of eliminating all stasis points and accelerating cancer cells to their fastest possible cycle times is unthinkable under today's protocols, and exactly the opposite approach is taken under prior art, where additional stasis points are added, such as concurrent administration of G-Phase cytostatics (e.g. HER blockers) with cell cycle active cytotoxics. Present invention's goal of elimination of all stasis points (to allow S-Phase cytotoxics to be synchronous) is exactly opposite to the prior art protocols disclosed in the specifications. As such, a prima facie case for unobviousness can be made.

I claim:

1. A method of progressively reducing the size of a tumor or tumors over expressing human epidermal growth factor receptor proteins (HER1 tumors) comprising interlaced administrations of S-Phase specific cell cycle active cytotoxic chemotherapeutic or chemotherapeutics in therapeutically effective amounts to reduce tumor size and HER1 blocker or blockers in therapeutically effective amounts to inhibit tumor regrowth between successive administrations of said S-Phase specific cell cycle active cytotoxic chemotherapeutic or chemotherapeutics and for a period of time that does not interfere with the utility of successive administrations of said S-Phase specific cell cycle active cytotoxic chemotherapeutic or chemotherapeutics.

2. The method of claim 1 wherein said HER1 blocker is erlotinib.

3. The method of claim 1 wherein said HER1 blocker is cetuximab.

4. The method of claim 1 wherein said HER1 blocker is gefitinib.

5. The method of claim 1 wherein when said HER1 tumor or tumors are also estrogen, progesterone, or testosterone dependent then estrogen, progesterone or testosterone is administered at a point in time prior to, or concurrent with, or both prior to and concurrent with, administration of said S-Phase specific cell cycle active cytotoxic chemotherapeutic or chemotherapeutics in therapeutically effective amounts to insure progression of said estrogen, progesterone, or testosterone dependent tumor or tumors through the cell cycle.

6. The method of claim 1 wherein when said HER1 tumor or tumors are also estrogen, progesterone, or testosterone dependent then estrogen, progesterone or testosterone blockers or downregulators are administered in conjunction with said HER1 blocker or blockers in therapeutically effective amounts to inhibit progression of said estrogen, progesterone, or testosterone dependent tumor or tumors through the cell cycle and estrogen, progesterone, or testosterone is administered at a point in time prior to, or concurrent with, or both prior to and concurrent with, administration of said S-Phase specific cell cycle active cytotoxic chemotherapeutic or chemotherapeutics in therapeutically effective amounts to insure progression of said estrogen, progesterone, or testosterone dependent tumor or tumors through the cell cycle.

7. The method of claim 1 wherein the VEGF blocker bevacizumab is administered in therapeutically effective amounts to prevent blood vessel cells from progressing through the cell cycle and said VEGF blocker bevacizumab is administered a point in time sufficiently prior to administration of said S-Phase specific cell cycle active chemotherapeutic or chemotherapeutics to prevent said blood vessel cells from being in the S-Phase of the cell cycle during administration of said S-Phase specific cell cycle active cytotoxic chemotherapeutic or chemotherapeutics.

* * * * *